(12) United States Patent
Habi et al.

(10) Patent No.: US 9,636,363 B2
(45) Date of Patent: *May 2, 2017

(54) HALOGENATED RHODAMINE DERIVATIVES AND APPLICATIONS THEREOF

(71) Applicant: KIADIS PHARMA CANADA INC., Saint Laurent (CA)

(72) Inventors: Abdelkrim Habi, Pierrefonds (CA); Denis Gravel, Saint-Lambert (CA); Luc Villeneuve, Montreal (CA); Hongsheng Su, Beaconsfield (CA); Marc Vaillancourt, Chateauguay (CA)

(73) Assignee: Kiadis Pharma Canada Inc., Saint Lambert, QC (CA)

(*) Notice: Subject to any disclaimer, the term of this patent is extended or adjusted under 35 U.S.C. 154(b) by 0 days.

This patent is subject to a terminal disclaimer.

(21) Appl. No.: 13/752,204

(22) Filed: Jan. 28, 2013

(65) Prior Publication Data
US 2014/0314720 A1 Oct. 23, 2014

Related U.S. Application Data

(60) Continuation of application No. 13/157,105, filed on Jun. 9, 2011, now Pat. No. 8,383,672, which is a
(Continued)

(30) Foreign Application Priority Data

Apr. 2, 2001 (CA) .................................. 2342675

(51) Int. Cl.
*A61K 35/28* (2015.01)
*C07D 311/82* (2006.01)
*A61K 35/14* (2015.01)

(52) U.S. Cl.
CPC .............. *A61K 35/28* (2013.01); *A61K 35/14* (2013.01); *C07D 311/82* (2013.01)

(58) Field of Classification Search
CPC ...................................................... A61K 35/28
(Continued)

(56) References Cited

U.S. PATENT DOCUMENTS 5,360,734 A * 11/1994 Chapman et al. ............ 435/238
5,556,992 A * 9/1996 Gaboury et al. ............. 549/227
(Continued)

FOREIGN PATENT DOCUMENTS

WO WO 00/17650 * 3/2000 .................... 549/227

OTHER PUBLICATIONS

Abrahart Dyes and their Intermediates pp. 225-227.*
(Continued)

*Primary Examiner* — Taofiq A Solola
(74) *Attorney, Agent, or Firm* — O'Melveny & Myers LLP

(57) ABSTRACT

Methods for treating an infection in a tissue sample are described. Tissue samples that are harvested from a patient may be infected with either bacteria or a virus. A rhodamine compound is mixed with the infected tissue sample to form a mixture. The mixture is then exposed to radiant energy to inhibit or kill the bacteria. The exposed mixture is then transplanted into the patient. The rhodamine compounds may be 2'-(6-dimethylamino-3-dimethylimino-3H-xanthen-9-yl) 4', 5'-dichloro-benzoic acid methyl ester hydrochloride.

9 Claims, 18 Drawing Sheets

General synthesis of substituted 4 and 2,7 halogenated rhodamine derivatives

Related U.S. Application Data continuation of application No. 12/786,280, filed on May 24, 2010, now abandoned, which is a continuation of application No. 12/403,819, filed on Mar. 13, 2009, now abandoned, which is a division of application No. 10/297,088, filed as application No. PCT/CA02/00438 on Mar. 27, 2002, now Pat. No. 7,560,574.

(58) Field of Classification Search
USPC .................................. 549/227; 514/454, 455
See application file for complete search history.

(56) References Cited

U.S. PATENT DOCUMENTS 5,773,460 A * 6/1998 Gaboury et al. .............. 514/454
8,383,672 B2 * 2/2013 Habi et al. .................... 514/455

OTHER PUBLICATIONS

Pal et al Photochem. & Photobio. vol. 63 No. 2 pp. 161-168 (1996).*
Chourasia et al "Antibacterial activity of rhodamines" Indian Drugs (1988), 25(4), 136-9 (abstract provided).*

* cited by examiner

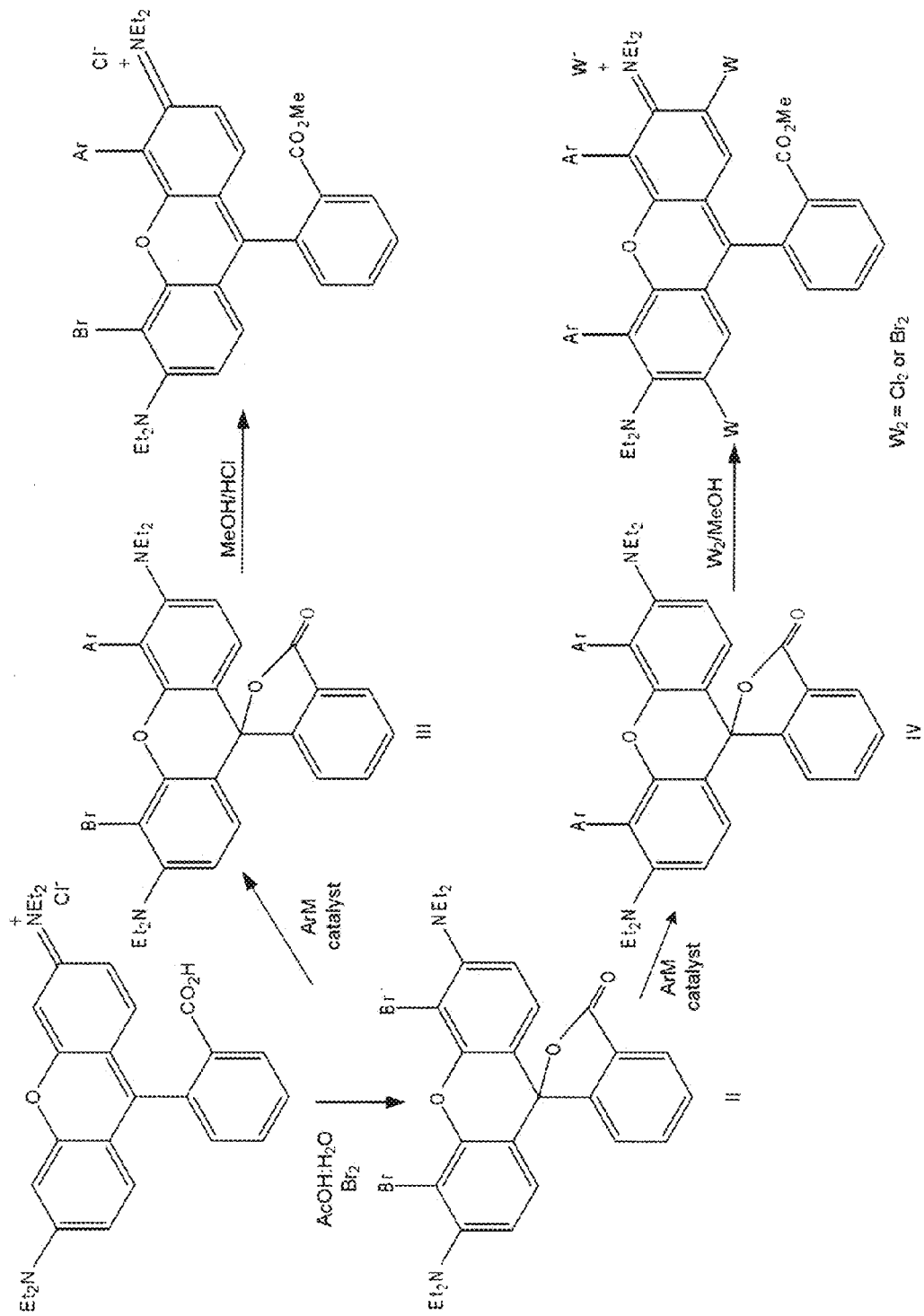
FIGURE 1: General synthesis of substituted 4 and 2,7 halogenated rhodamine derivatives

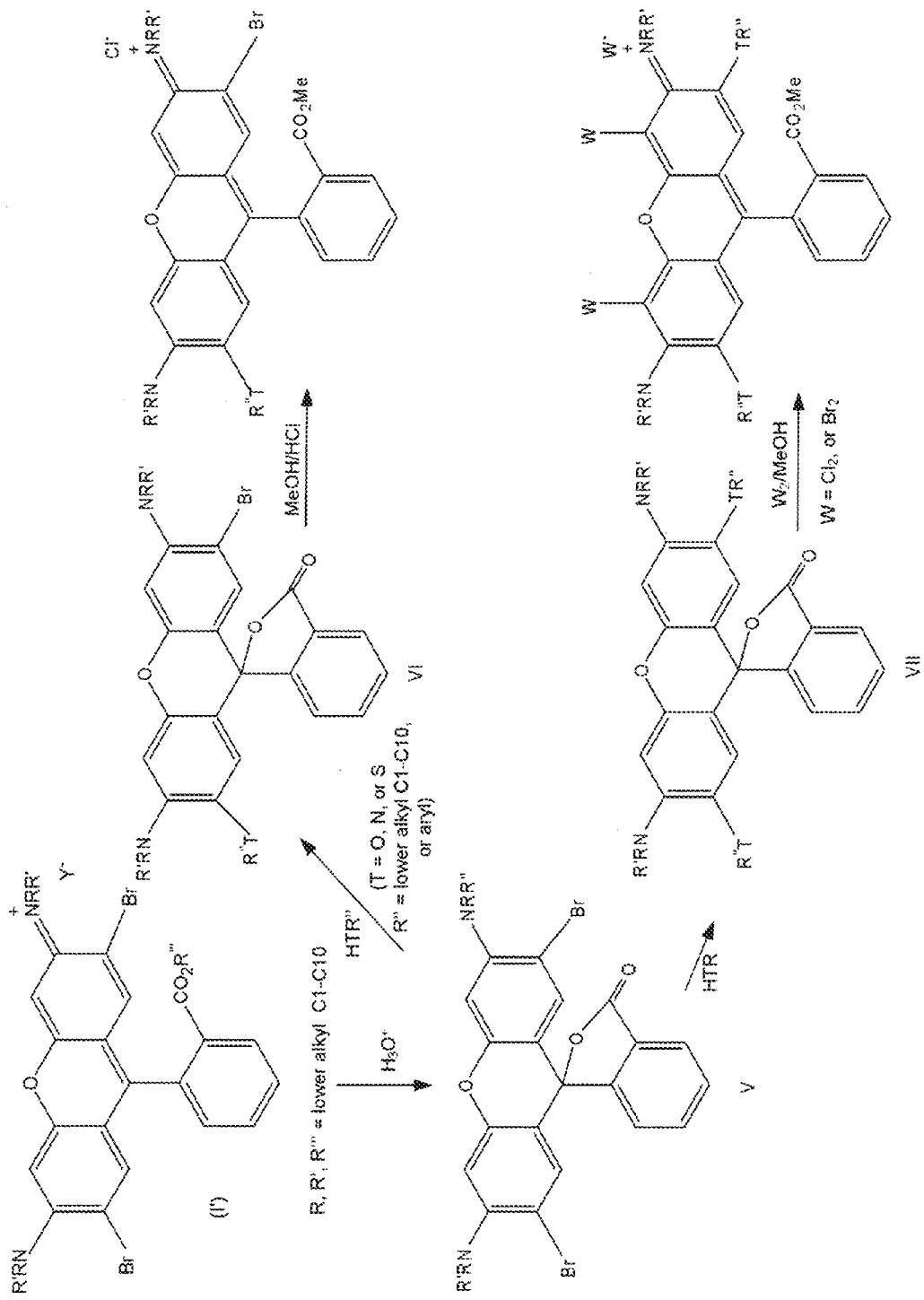
FIGURE 2: General synthesis of substituted 2 and 4,5 halogenated rhodamine derivatives

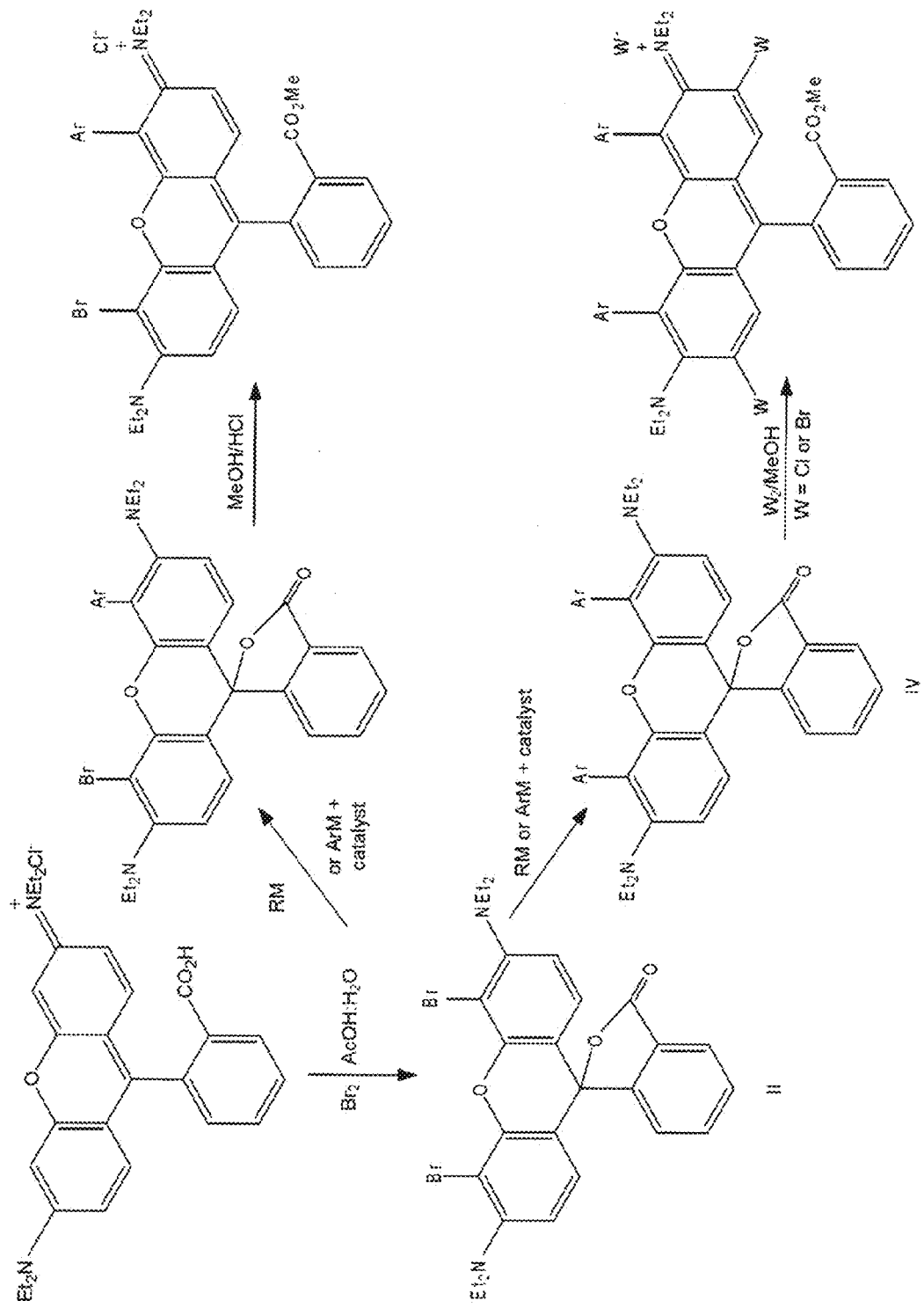
FIGURE 3: General synthesis of substituted 4- and 2,7-halogenated rhodamine derivatives

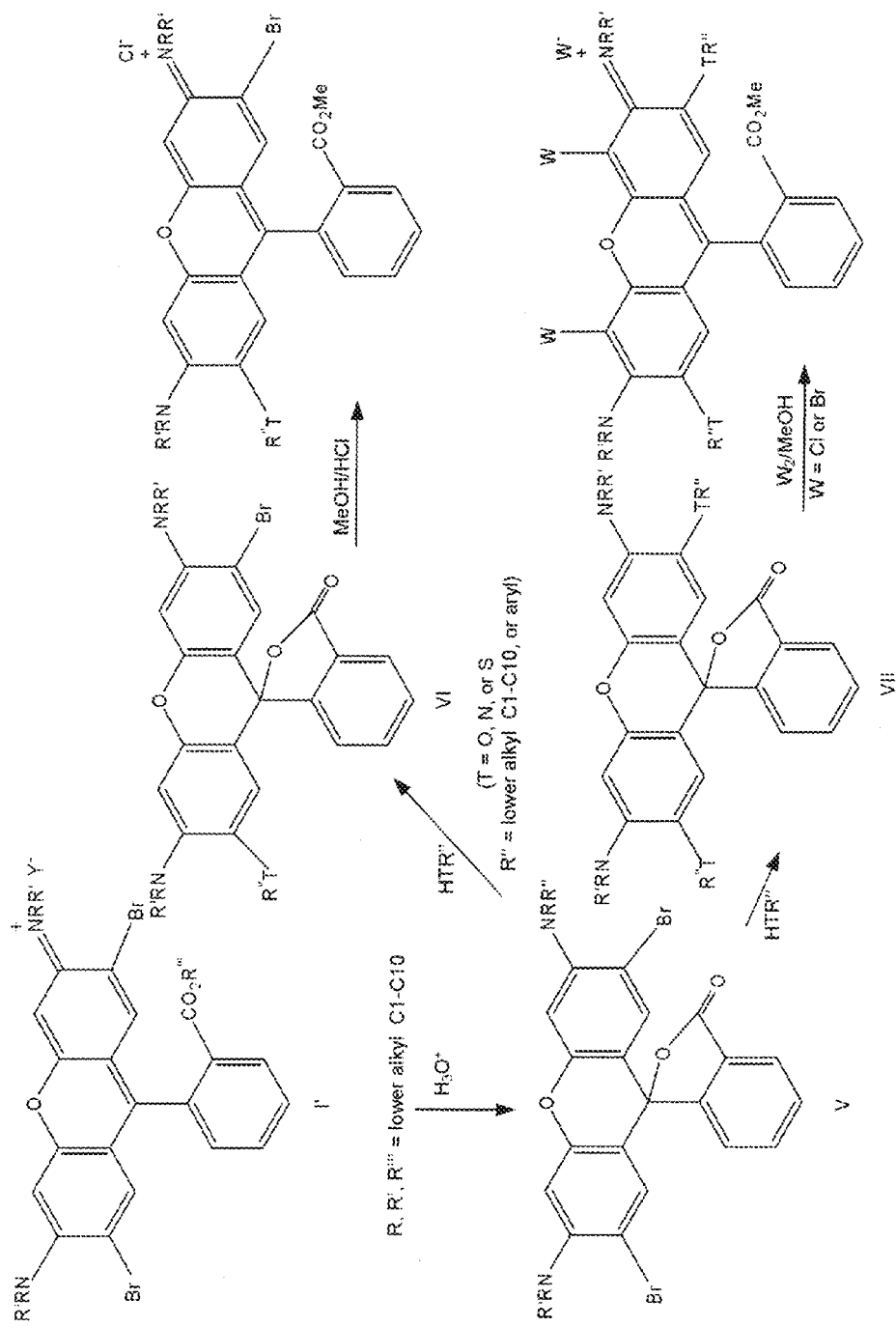
FIGURE 4: General synthesis of substituted 2- and 4,5-halogenated rhodamine derivatives

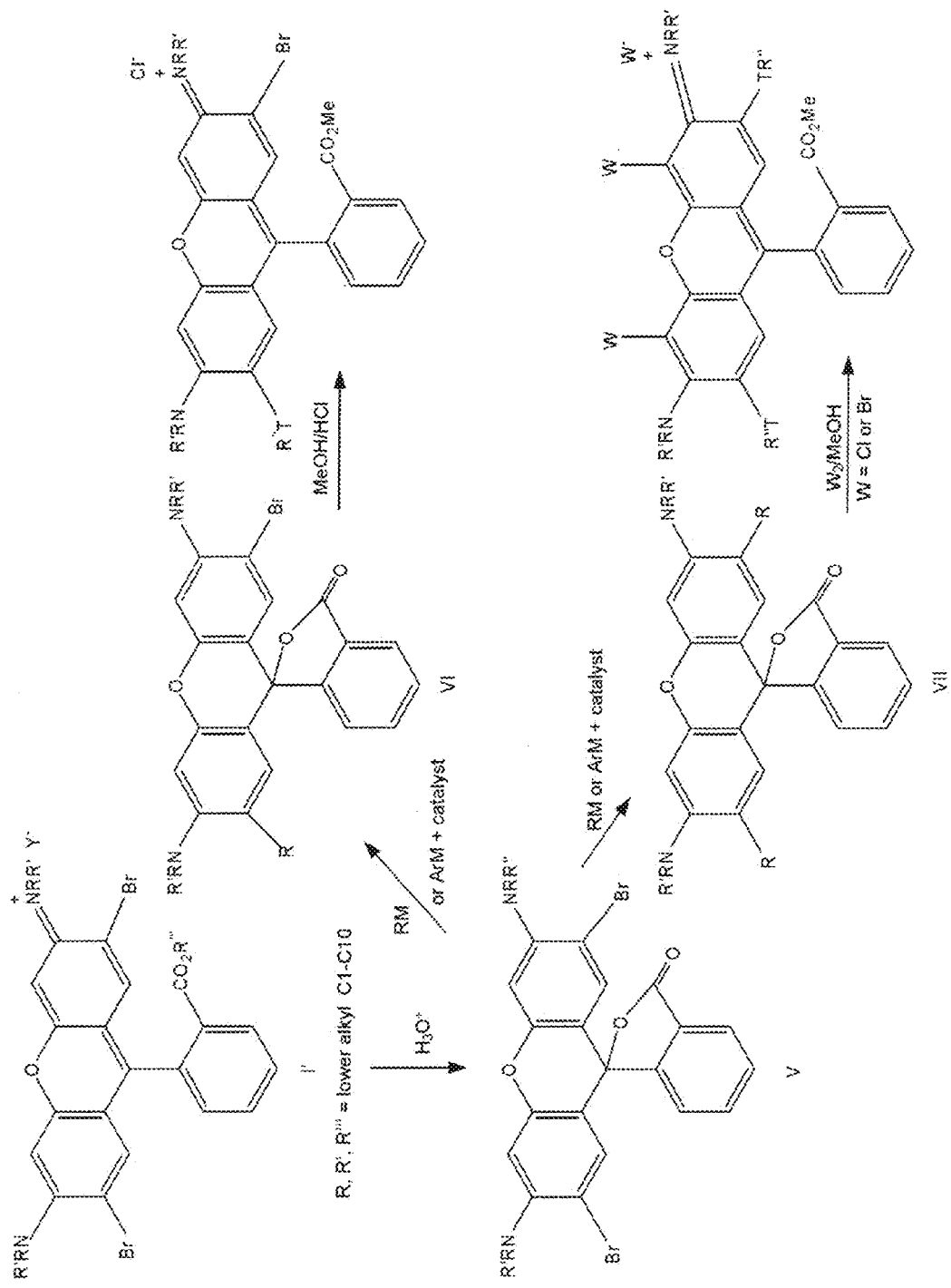
FIGURE 5: General synthesis of substituted 2- and 4,5-halogenated rhodamine derivatives

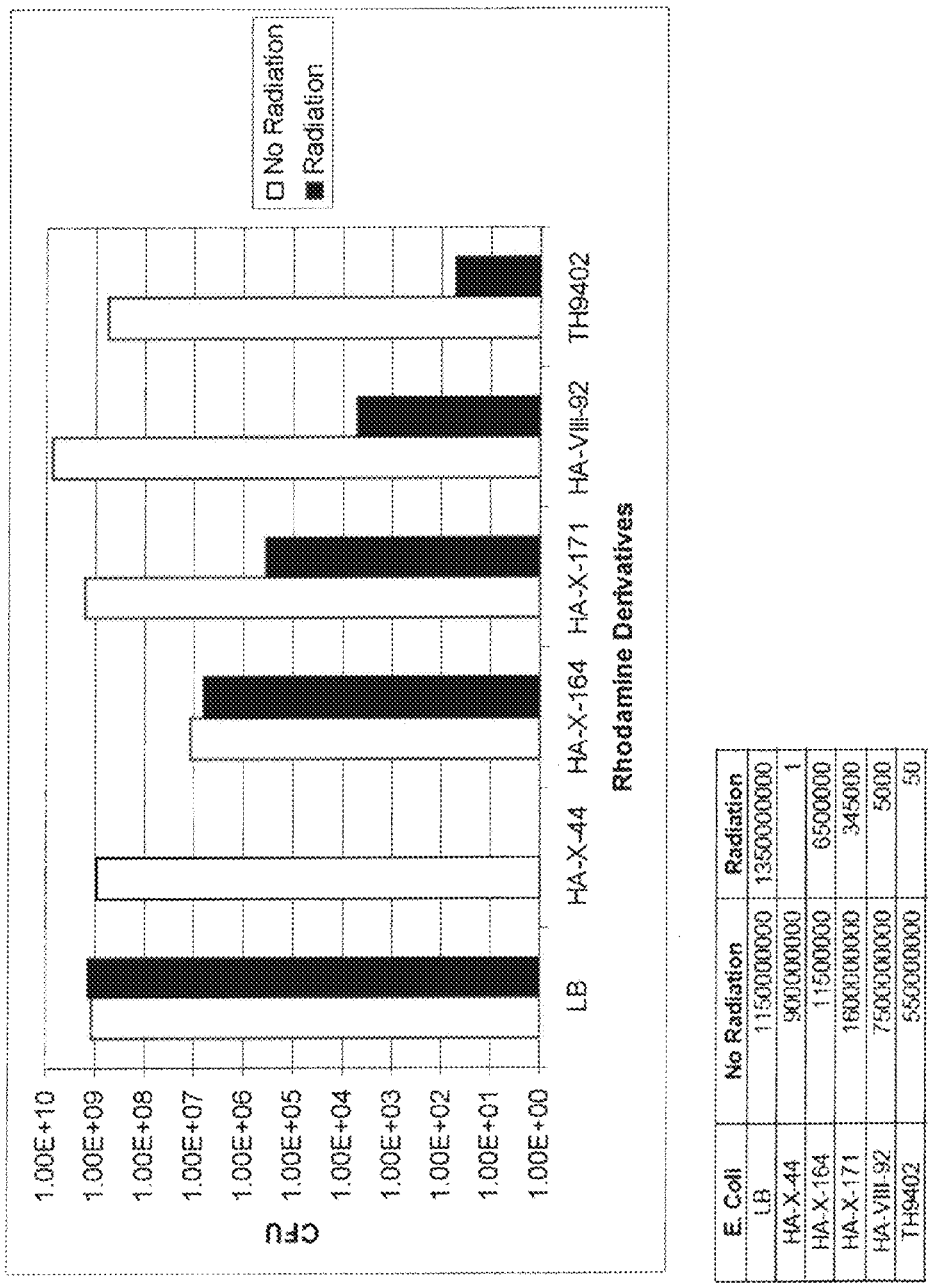
FIGURE 6: Bacteriostatic activity of rhodamine derivatives against E. coli

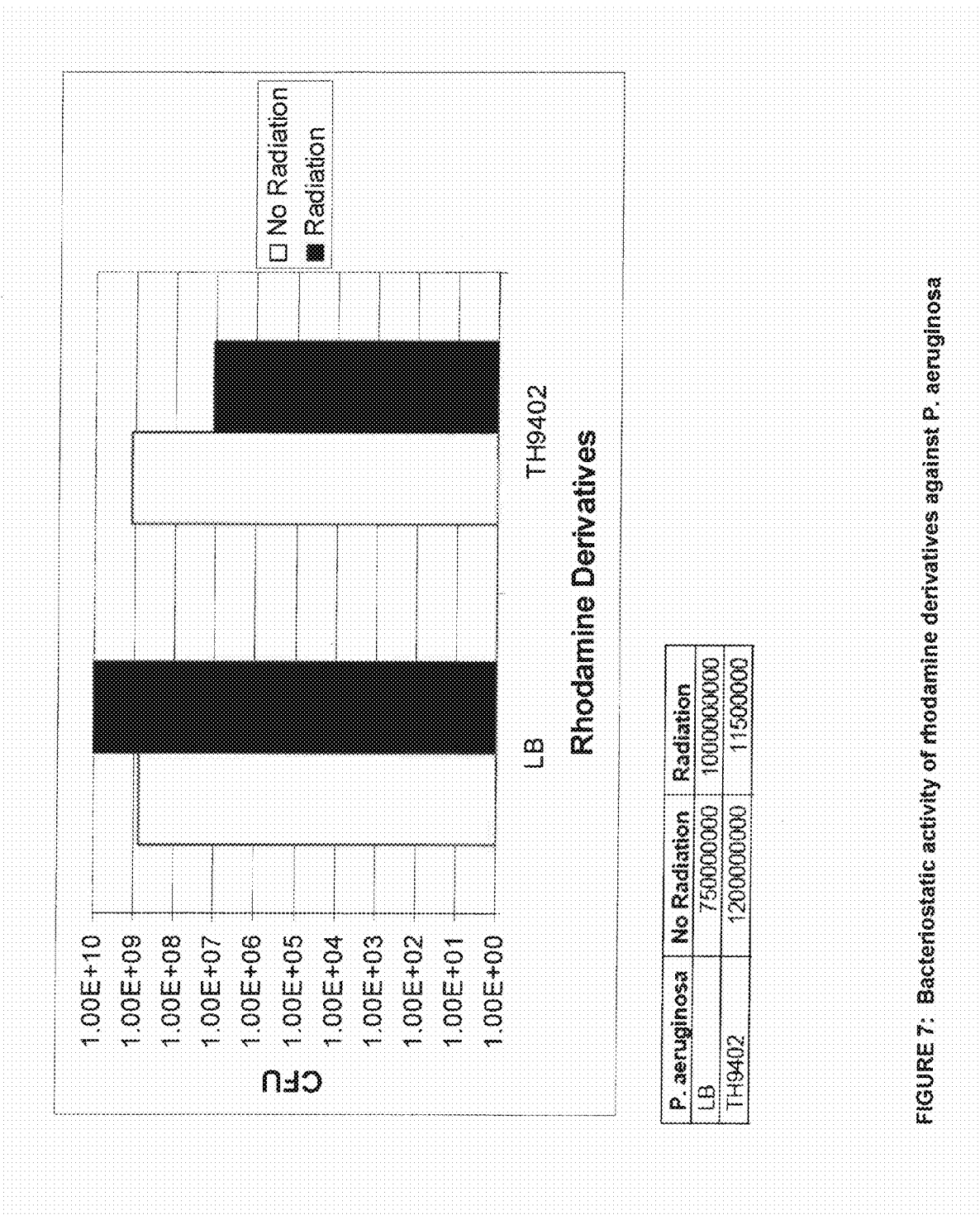
FIGURE 7: Bacteriostatic activity of rhodamine derivatives against P. aeruginosa

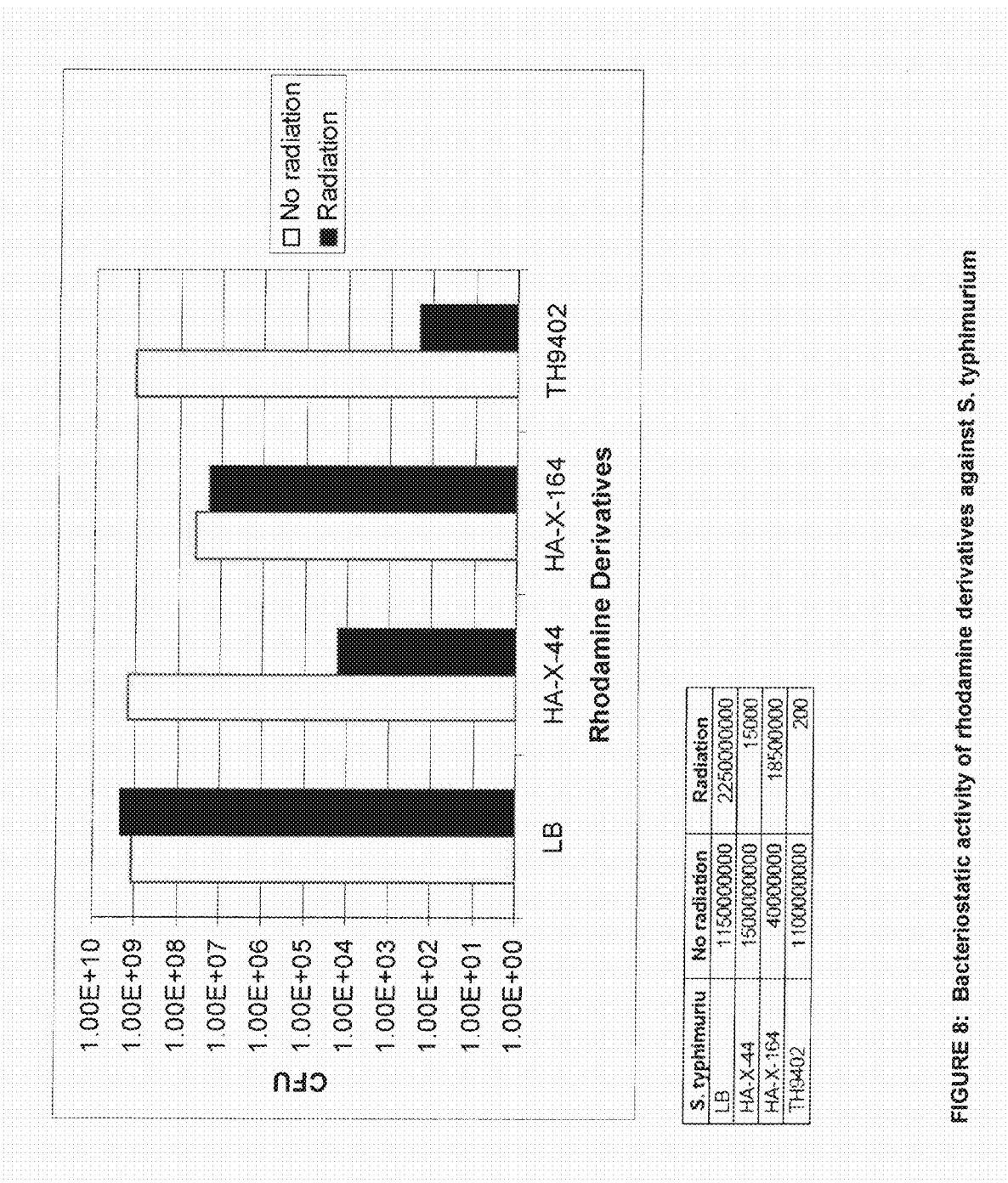
FIGURE 8: Bacteriostatic activity of rhodamine derivatives against S. typhimurium

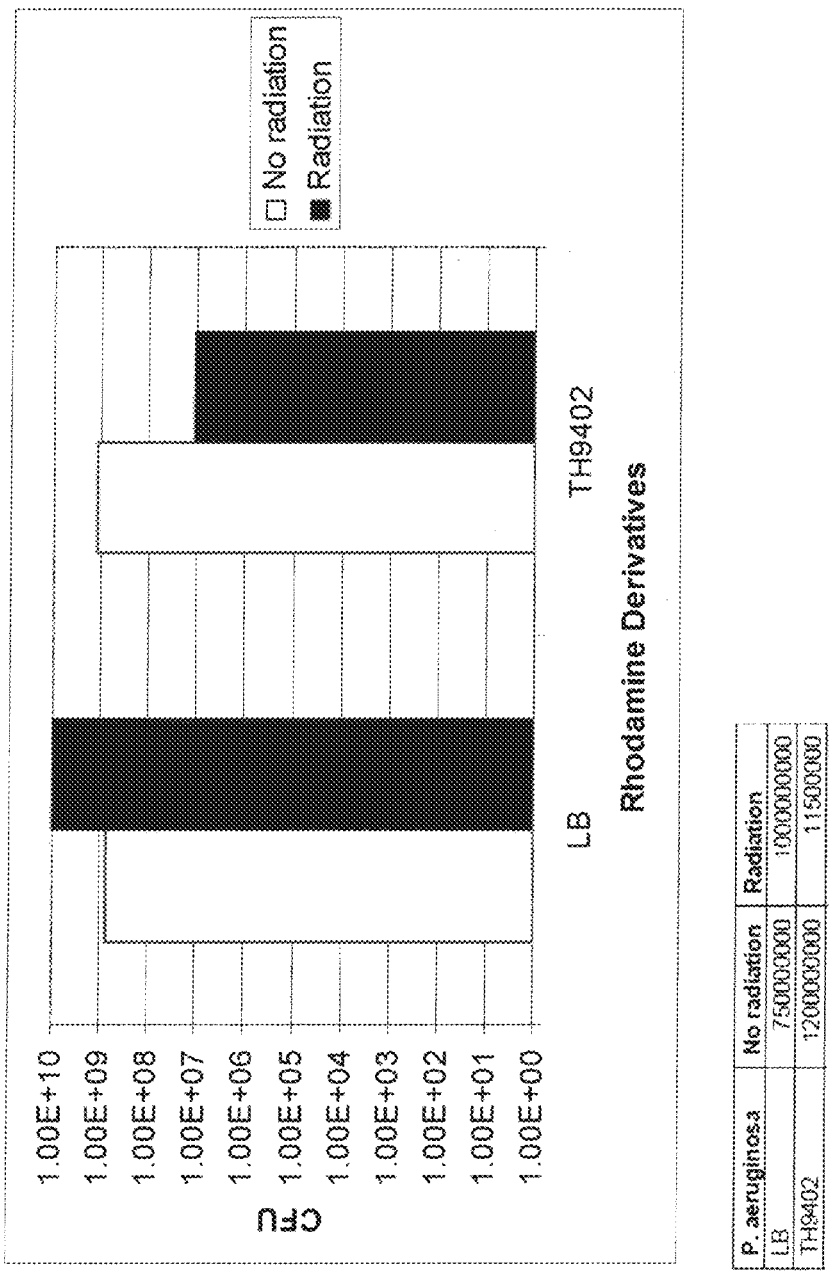
FIGURE 9: Bacteriostatic activity of rhodamine derivatives against P. aeruginosa Log decreases of viral infectivity and proliferation in FS cells

| | |
|---|---|
| HA-X-40 | 3 logs |
| HA-X-149 | 3 logs |
| HA-X-164 | 0, 5-1,0 log |
| HA-X-171 | 1,5-1,0 log |
| HA-VIII-92 | 3 logs |

Log decreases of viral infectivity and proliferation in FS cells

| | |
|---|---|
| HA-X-44 | eradication |
| TH9402 | eradication |

FIGURE 10: Antiviral activity of rhodamine derivatives tested on cytomegalovirus

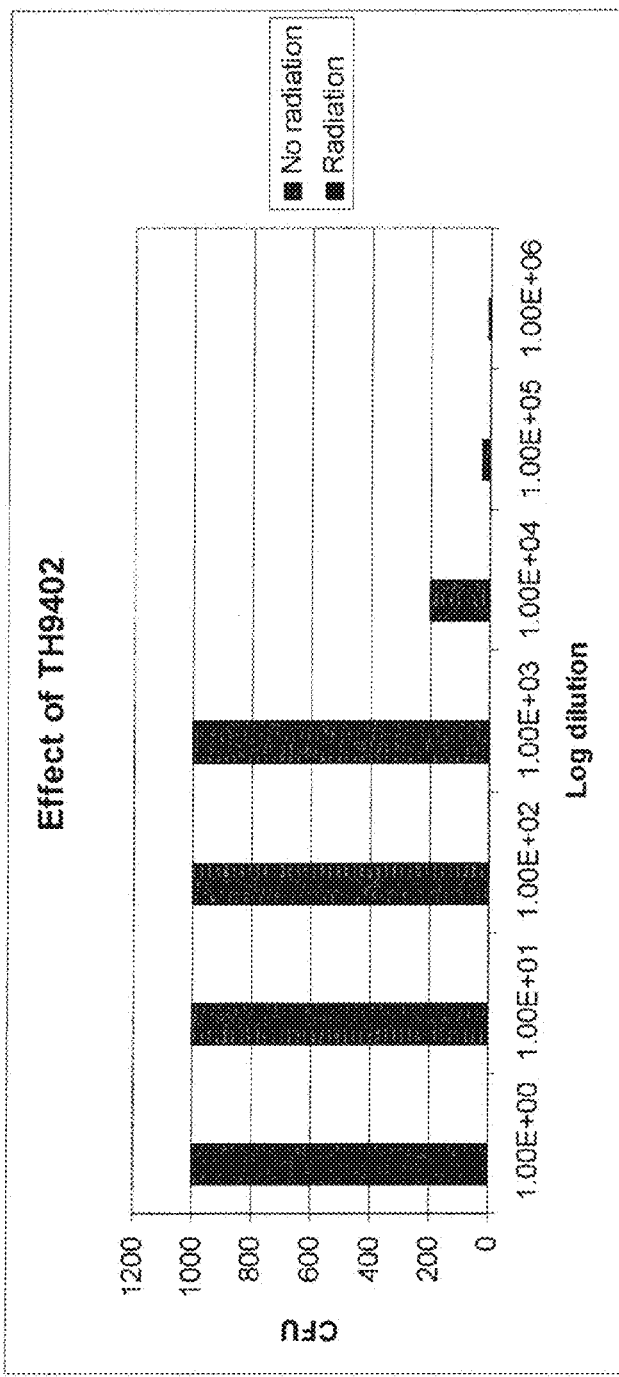
FIGURE 11: Staphilococcus epidermitis

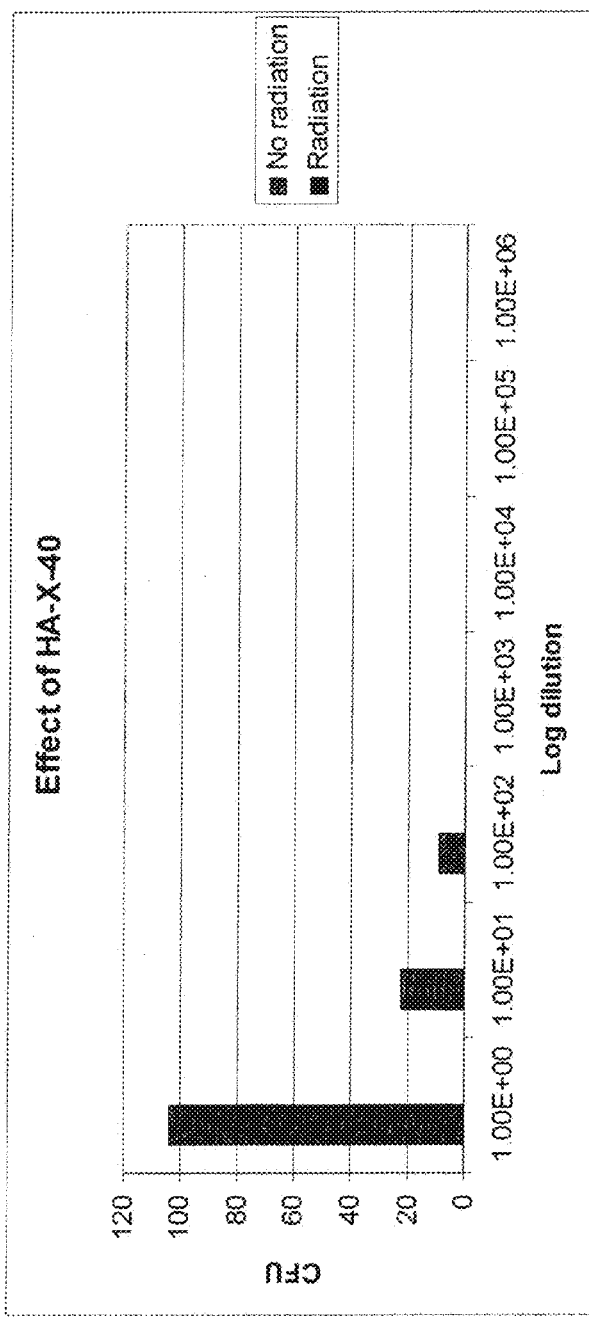
FIGURE 12: Staphilococcus epidermitis

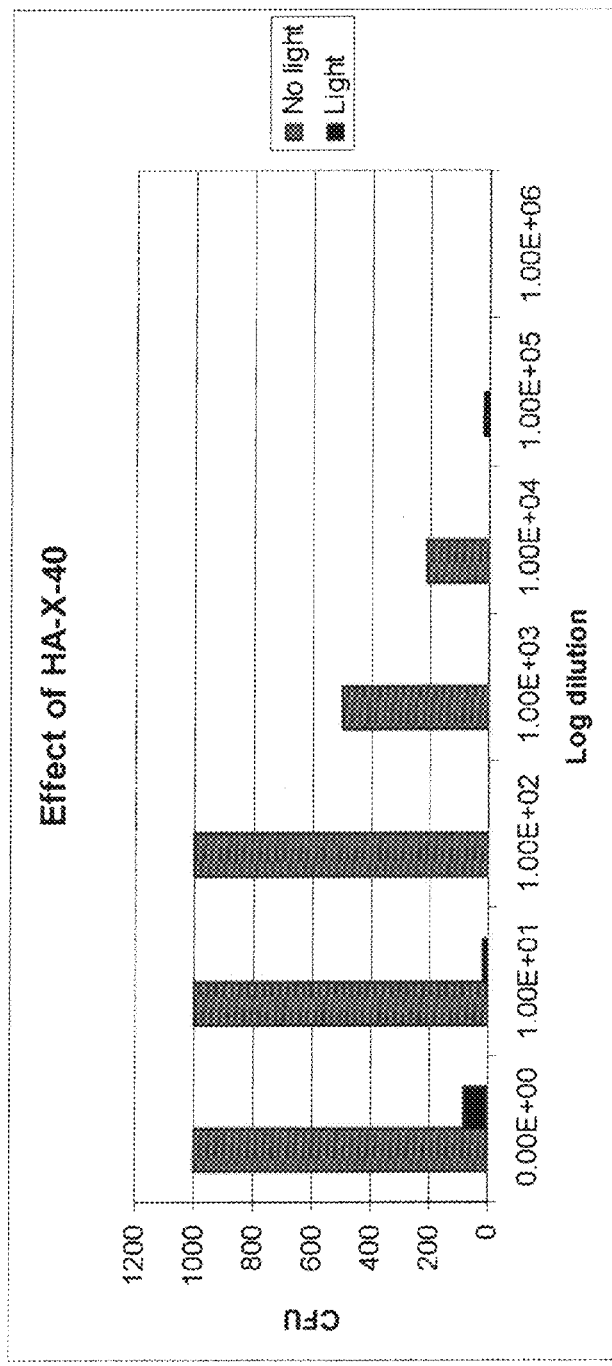
FIGURE 13: Staphilococcus epidermitis

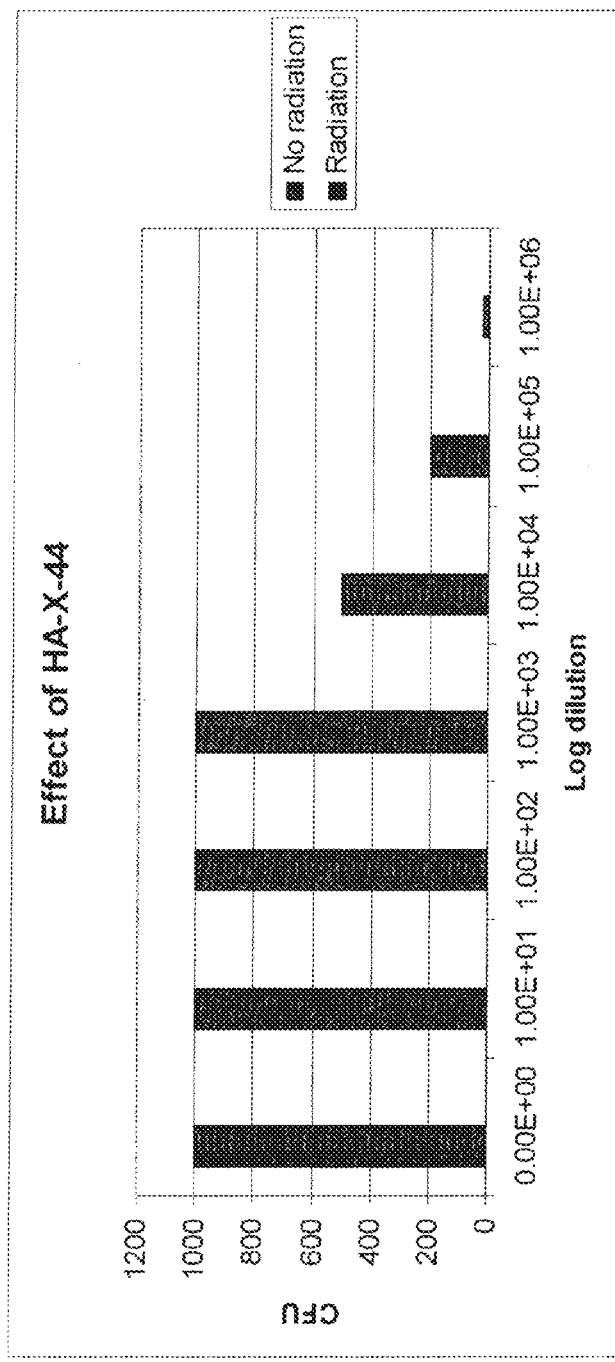
FIGURE 14: Staphilococcus epidermitis

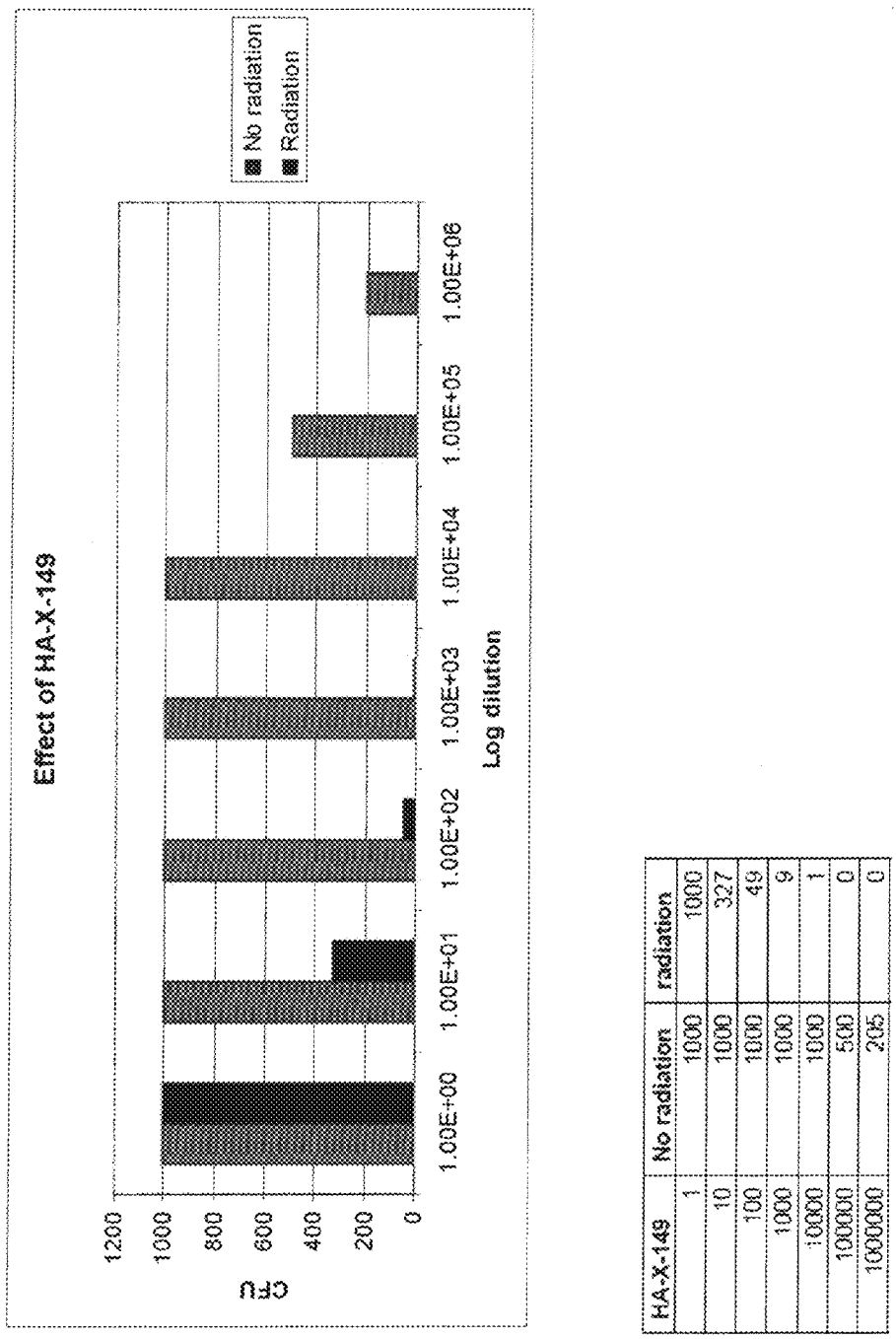
FIGURE 15: Staphilococcus epidermitis

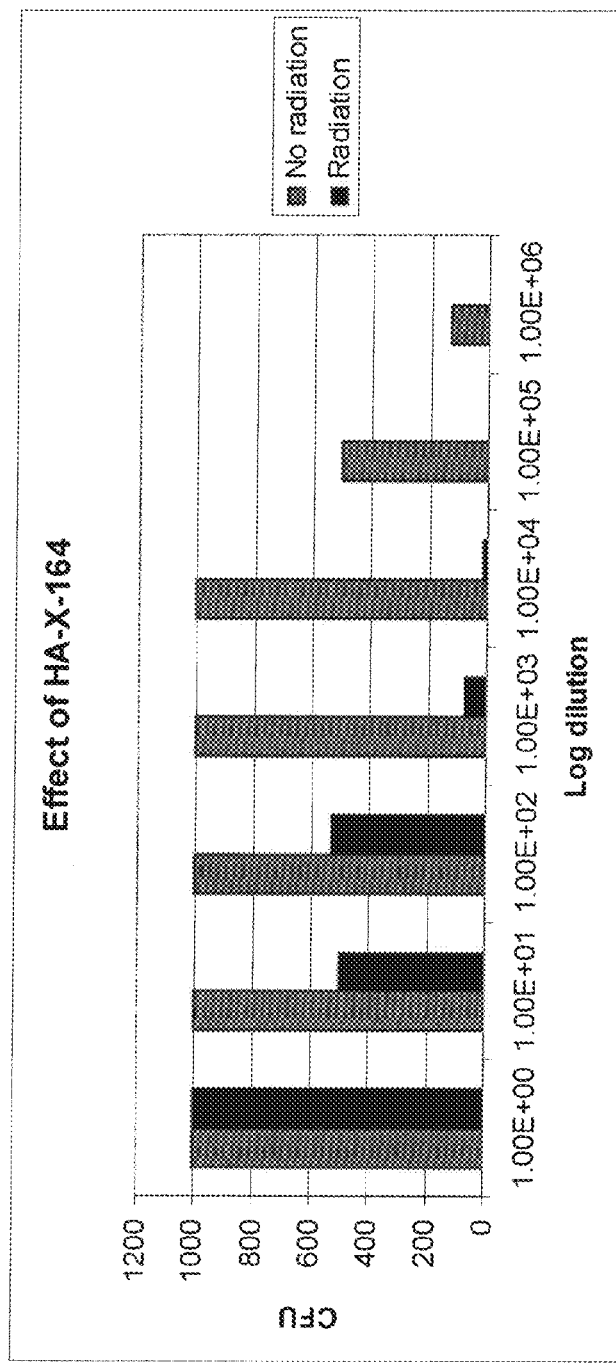
FIGURE 16: Staphilococcus epidermitis

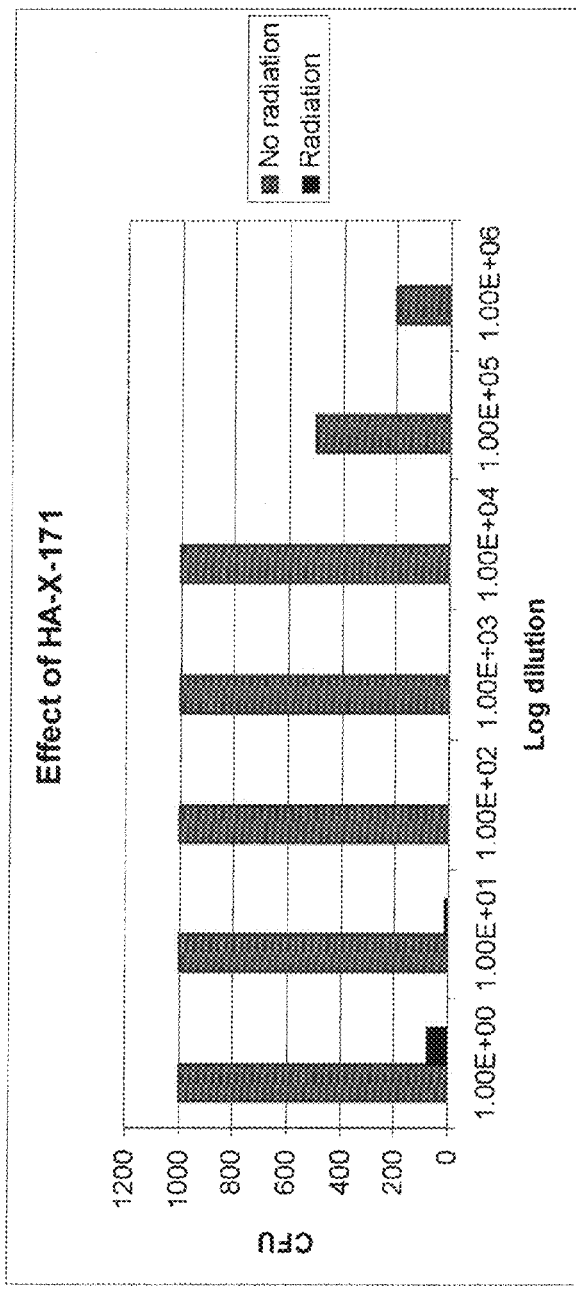
FIGURE 17: Staphilococcus epidermitis

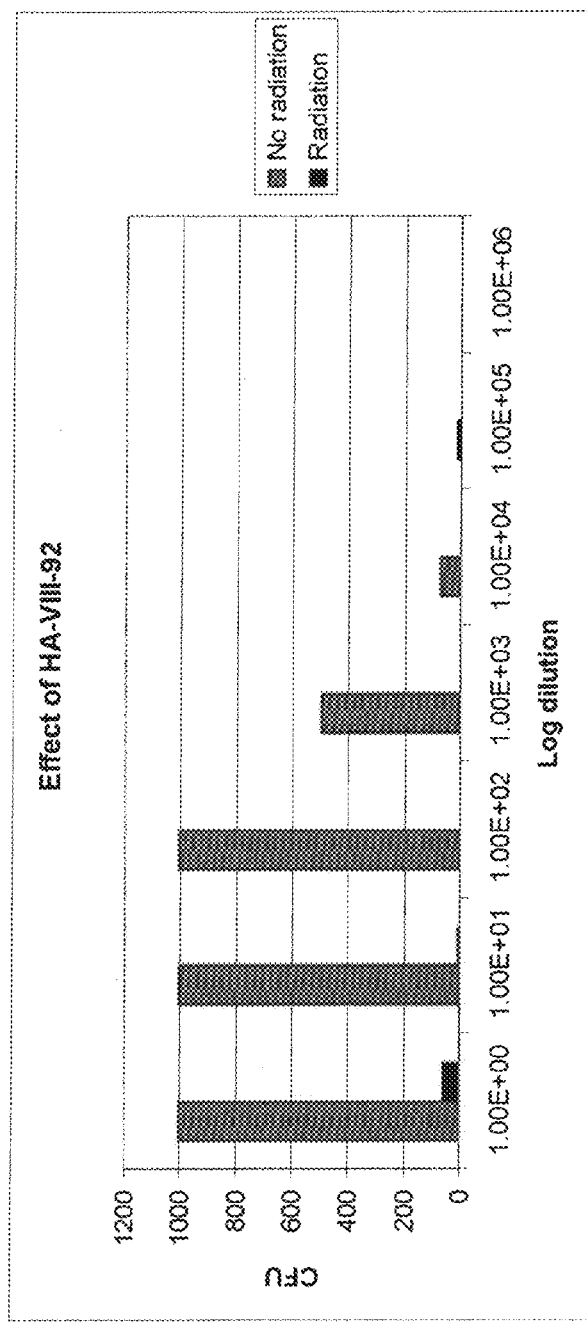
FIGURE 18: Staphilococcus epidermitis

HALOGENATED RHODAMINE DERIVATIVES AND APPLICATIONS THEREOF

CROSS REFERENCE TO RELATED APPLICATIONS

This is a continuation of U.S. application Ser. No. 13/157,105, filed Jun. 9, 2011, which is a continuation of U.S. application Ser. No. 12/786,280, filed May 24, 2010, now abandoned, which is a continuation of U.S. application Ser. No. 12/403,819, filed Mar. 13, 2009, now abandoned, which is a division of U.S. application Ser. No. 10/297,088, filed May 30, 2003, now issued as U.S. Pat. No. 7,560,574, which in turn is a national stage application of international application no. PCT/CA02/00438, filed Mar. 27, 2002, which in turn claims priority to Canadian Application No. 2,342,675 and U.S. application Ser. No. 09/822,223, both filed Apr. 2, 2001. All of the above applications are expressly incorporated herein by reference in their entirety for all purposes.

FIELD OF THE INVENTION

The invention relates to new rhodamine derivatives that are useful for their pharmaceutical and non-pharmaceutical properties.

The rhodamine derivatives of the invention exhibit powerful bactericidal and antiviral activities.

They are also useful, alone or in association with a pharmaceutically acceptable carrier, in the treatment and/or in the prevention of immunologic disorders.

Moreover, those derivatives are useful as intermediates I the synthesis of further new rhodamine derivatives and also in the new synthesis of already known rhodamine derivatives.

Finally, the present invention also relates to new processes for the preparation of rhodamine derivatives.

BACKGROUND OF THE INVENTION

Photodynamic therapy has been used as a method for the eradication of neoplastic cells from autologous grafts for cancer treatments. This method relies on the use of photosensitizing dyes, which when activated with light of a particular wavelength, produce toxic $O_2$ radicals, ultimately leading to cell death. Photochemical treatments have also been used for pathogen inactivation, such as in "decontamination" of blood and blood-derived products. The danger of pathogen transmission through transfusion of whole blood, platelets concentrates, plasma and/or red blood cells still represent major concerns in medicine. Although there has been impressive progress in the prevention and maintenance of blood safety regarding the presence of microorganisms, blood components continue to carry risk of pathogen transfusion. Moreover, the presence of viruses in blood components is also of great concerns, mainly for the presence of Hepatitis C and human immunodeficiency virus (HIV), even though the risk of contamination is reduced to negligible levels. The presence of other viruses is also required and includes the human T-cell lymphotrophic virus type 1 (HTLV-1), Hepatitis B (HBV) and cytomegalovirus. Photodynamic compounds such as pseuralens, porphyrines, riboflavines and dimethyl of methylene bleue have been used in the treatment of pathogen in blood product. These compounds necessitate radiation by a ultra violet A lamp (UVA) to get activated, thus leading to possible mutagenic effect in the remaining cells present in the treated samples. (Corash, L., Inactivation of infectious pathogens in labile blood components: meeting the challenge, Transfus Clin Biol, 2001, 8, 138-145 Lin, L., Londe, H., Janda, M. J., Hanson, C. V. and Corash, L., Photochemical inactivation of pathogenic bacteria in human platelet concentrates, Blood, 1994, 83, 9, 2698-2706; Lin, L, Londe, H., Hanson, C. V., Wiesehahn, G., Isaacs, S., Cimino, G. and Corash, L., Photochemical inactivation of cell-associated human immunodeficiency virus in platelet concentrates, Blood, 1993, 82, 1, 292-297; Lin, L., Eiesehahn, G. P., Morel, P. A. and Corash, L., Use of 8-methoxypsoralen and long-wavelength ultraviolet radiation for decontamination of platelet concentrates, Blood, 1989, 74, 1, 517-525; Lin, L., Cook, D. N., Wiesehahn, G. P., Alfonso, R., Behrman, B., Cimino, G. D., Corten, L., Damonte, P. B., Dikeman, R., Dupuis, K., Fang. Y. M., Hanson, C. V., Heasrt, J. E., Lin, C. Y., Londe, H., Metchette, K., Nerio, A. T., Pu, J. T., Reames, A. A., Rheinschmidt, M., Tessman, J., Isaacs, S. T., Wollowitz, S. and Corash, L., Photochemical inactivation of viruses and bacteria in platelet concentrates by use of a novel psoralen and long-wavelength ultraviolet light, Transfusion, 1997, 37, 423-435). Because of the UVA exposure to blood components, these techniques are not entirely satisfactory. There was therefore a need for new light sensitive derivatives that do not necessitate UVA exposure of blood components and that may also be a safer ad more acceptable replacement to UVA treated blood components.

Immunologic disorders are uncontrolled cell proliferations that result from the production of immune cells recognizing normal cells and tissues as foreign. After a variable latency period during which they are clinically silent, cells with immunoreactivity towards normal cells induce damages in these normal cells and tissues. Such immunologic disorders are usually divided in alloimmune conditions and autoimmune conditions. Alloimmune disorders occur primarily in the context of allogeneic transplantation (bone marrow and other organs: kidney, heart, liver, lung, etc.). In the setting of bone marrow transplantation, donor immune cells present in the hematopoietic stem cell graft react towards host normal tissues, causing graft-versus-host disease (GVHD). The GVHD induces damage primarily to the liver, skin, colon, lung, eyes and mouth. Autoimmune disorders are comprised of a number of arthritic conditions, such as rhumatoid arthritis, scleroderma and lupus erythematosus; endocrine conditions, such as diabetes mellitus; neurologic conditions, such as multiple sclerosis and myasthenia gravis; hematological disorders, such as autoimmune hemolytic anemia, etc. The immune reaction, in both alloimmune and autoimmune disorders, progresses to generate organ dysfunction and damage.

Despite important advances in treatment, immunologic complications remain the primary cause of failure of allogeneic transplantations, whether in hematopoietic stem cell transplantation (GVHD) or in solid organ transplantation (graft rejection). In addition, autoimmune disorders represent a major cause of both morbidity and mortality. Prevention and treatment of these immune disorders has relied mainly on the use of immunosuppressive agents, monoclonal antibody-based therapies, radiation therapy, and more recently molecular inhibitors. Significant improvement in outcome has occurred with the continued development of combined modalities, but for a small number of disorders and patients. However, for the most frequent types of transplantations (bone marrow, kidney, liver, heart and lung), and for most immune disorders (rheumatoid arthritis, connective tissue diseases, multiple sclerosis, etc.) resolution of the immunologic dysfunction and cure has not been achieved. Therefore, the development of new approaches for the prevention and treatment of patients with immunologic disorders is critically needed particularly for those patients who are at high risk or whose disease has progressed and are refractory to standard immunosuppressive therapy. Allogeneic stem cell transplantation (AlloSCT) has been employed for the treatment of a number of malignant and non-malignant conditions. Allogeneic stem cell transplantation is based on the administration of high-dose chemotherapy with or without total body irradiation to eliminate malignant cells, and host hematopoietic cells. Normal hematopoietic donor stem cells are then infused into the patient in order to replace the host hematopoietic system. AlloSCT has been shown to induce increased response rates when compared with standard therapeutic options. One important issue that needs to be stressed when using AlloSCT relates to the risk of reinfusing immune cells that will subsequently recognize patient cells as foreign and cause GVHD. A variety of techniques have been developed that can deplete up to $10^5$ of T cells from the marrow or peripheral blood. These techniques, including immunologic and pharmacologic purging, are not entirely satisfactory. One major consideration when purging stem cell grafts is to preserve the non-host reactive T cells so that they can exert anti-infectious and anti-leukemia activity upon grafting. The potential of photodynamic therapy, in association with photosensitizing molecules capable of destroying immunologically reactive cells while sparing normal host-non-reactive immune cells, to purge hematopoietic cell grafts in preparation for AlloSCT or autologous stem cell transplantation (AutoSct), and after AlloSCT in the context of donor lymphocyte infusions to eliminate recurring leukemia cells has largely been unexplored. To achieve eradication of T cells, several approaches have been proposed including:

1) in vitro exposure of the graft to monoclonal antibodies and immunotoxins against antigens present on the surface of T cells (anti-CD3, anti-CD6, anti-CD8, etc.);
2) in vitro selection by soybean agglutinin and sheep red blood cell rosetting;
3) positive selection of CD34+ stem cells; and
4) in vivo therapy with combinations of anti-thymocyte globulin, or monoclonal antibodies.
5) In vitro exposure of recipient-reactive donor T cells by monoclonal antibodies or immunotoxins targeting the interleukin 2 receptor or OX-40 antigen (Cavazzana-Calvo M. et al. (1990) Transplantation, 50:1-7; Tittle T. V. et al (1997) Blood 89:4652-58; Harris D. T. et al. (1999) Bone Marrow Transplantation 23:137-44).

However, most of these methods are not specifically directed at the alloreactive T cell subset and associated with numerous problems, including disease recurrence, graft rejection, second malignancies and severe infections. In addition, the clinical relevance of several of these methods remains to be established.

There are many reports on the use of photodynamic therapy in the treatment of malignancies (Daniell M. D., Hill J. S. (1991) *Aust. N. Z J Surg.*, 61: 340-348). The method has been applied for cancers of various origins and more recently for the eradication of viruses and pathogens (Raab O. (1990) *Infusoria Z. Biol.*, 39:524).

The initial experiments on the use of photodynamic therapy for cancer treatment using various naturally occurring or synthetically produced photoactivable substances were published early this century (Jesionek A., Tappeiner V. H. (1903) *Muench Med Wochneshr*, 47: 2042; Hausman W. (1911) *Biochem. Z.*, 30: 276). In the 40's and 60's, a variety of tumor types were subjected to photodynamic therapy both in vitro and in vivo (Kessel, David (1990) *Photodynamic Therapy of neoplastic disease*, Vol. I, II, CRC Press. David Kessel, Ed. ISBN 0-8493-5816-7 (v. 1), ISBN 0-8493-5817-5 (v. 2)). Dougherty et al. and others, in the 70's and 80's, systematically explored the potential of oncologic application of photodynamic therapy (Dougherty T. J. (1974) *J Natl Cancer Inst.*, 51: 1333-1336; Dougherty T. J. et al. (1975) *J. Natl Cancer Inst.*, 55: 115-121; Dougherty T. J. et al. (1978) *Cancer Res.*, 38: 2628-2635; Dougherty T. J. (1984) *Urol. Suppl.*, 23: 61; Dougherty T. J. (1987) *Photochem. Photobiol.*, 45: 874-889).

Treatment of Immunoreactive Cells with Photodynamic Therapy

There is currently a lack of agents which allow selective destruction of immunoreactive cells while leaving intact the normal but suppressed residual cellular population. Preferential uptake of photosensitive dye and cytotoxicity of photodynamic therapy against leukemia (Jamieson C. H. et al. (1990) *Leuk. Res.*, 14: 209-219) and lymphoid cells (Greinix H. T., et al. Blood (1998) 92:3098-3104; are reviewed in Zic J. A. et al. Therapeutic Apheresis (1999) 3:50-62) have been previously demonstrated.

It would be highly desirable to be provided with photosensitizers which possess at least one of the following characteristics:

i) preferential localization and uptake by the immunoreactive cells;
ii) upon application of appropriate light intensities, killing those cells which have accumulated and retained the photosensiting agents;
iii) sparing of the normal hemopoietic stem cell compartment from the destructive effects of activated photosensitizers; and
iv) potential utilization of photosensitizers for hematopoietic stem cell purging of immunoreactive cells, in preparation for allogeneic or autologous stem cell transplantation.
v) Potential utilization of photosensitizers for ex vivo elimination of reactive immune cells in patients with immunological disorders.

The Rhodamine Dyes

Rhodamine 123 (2-(6-amino-3-imino-3H-xanthen-9-yl) benzoic acid methyl ester hydrochloride), a lipophilic cationic dye of the pyrylium class which can disrupt cellular homeostasis and be cytostatic or cytotoxic upon high concentration exposure and/or photodynamic therapy, although with a very poor quantum yield (Darzynkiewicz Z., Carter S. (1988) *Cancer Res.*, 48: 1295-1299). It has been used in vitro as a specific fluorescent stain for living mitochondria. It is taken up and is preferentially retained by many tumor cell types, impairing their proliferation and survival by altering membrane and mitochondrial function (Oseroff A. R. (1992) In *Photodynamic therapy* (Henderson B. W., Dougherty T. J., eds) New York: Marcel Dekker, pp. 79-91). In vivo, chemotherapy with rhodamine 123 can prolong the survival of cancerous mice, but, despite initial attempts to utilize rhodamine 123 in the treatment of tumors, the systemic toxicity of rhodamine 123 may limit the usefulness (Bernal, S. D., et al. (1983) *Science*, 222: 169; Powers, S. K. et al. (1987) *J. Neurosur.*, 67: 889).

U.S. Pat. No. 4,612,007 issued on Sep. 16, 1986 in the name of Richard L. Edelson, discloses a method for externally treating human blood, with the objective of reducing the functioning lymphocyte population in the blood system of a human subject. The blood, withdrawn from the subject, is passed through an ultraviolet radiation field in the presence of a dissolved photoactive agent capable of forming photoadducts with lymphocytic-DNA. This method presents the following disadvantages and deficiencies. The procedure described is based on the utilization of known commercially available photoactive chemical agents for externally treating patient's blood, leaving the bone marrow and potential resident leukemic clones intact in the process. According to Richard L. Edelson, the method only reduces, does not eradicate, the target cell population. Moreover, the wavelength range of UV radiation used in the process proposed by Richard L. Edelson could be damageable to the normal cells.

International Application published on Jan. 7, 1993 under International publication number WO 93/00005, discloses a method for inactivating pathogens in a body fluid while minimizing the adverse effects caused by the photosensitive agents. This method essentially consists of treating the cells in the presence of a photoactive agent under conditions that effect the destruction of the pathogen, and of preventing the treated cells from contacting additional extracellular protein for a predetermined period of time. This method is concerned with the eradication of infectious agents from collected blood and its components, prior to storage or transfusion.

It would be highly desirable to be provided with new rhodamine derivatives for the treatment of immunereactive cells which overcomes these drawbacks while having no systemic toxicity for the patient.

Halogenated rhodamine salts are dyes that have the property of penetrating cells and generally localising at the mitochondria. They have been used in conjunction with photoactivation to kill certain types of cells, namely cancer cells in Leukemia, and activated T-cells in autoimmune diseases.

The generally accepted mechanism for the cell killing effect is the production of singlet oxygen which is the reactive intermediate in the disruption of the life-sustaining biological processes of the cell.

The role of the rhodamine dye in the production of singlet oxygen is that of a photosensitizer, i.e. that of a molecule which absorbs the incident light energy and transfers it to ground state oxygen, thereby elevating it to its singlet excited state which is the reactive intermediate.

It is further known that the efficiency of the energy transfer process is greatly enhanced by the presence of heavy atoms such as halogens on the aromatic chromophore of the dye.

One critical problem that has not been addressed however is the differential uptake of the photosensitizer by the target cells relative to the other, normal, cells. Indeed, it is known that uptake is generally a function of the molecular structure of the dye being absorbed and that this property varies with different cell types.

It would therefore be highly desirable to be provided with a series of new halogenated rhodamine dyes bearing a variety of substituents at different positions of the molecule thereby making available new selective dyes for specific target cells.

One aim of the present invention is to produce new photosensitizers endowed with the following characteristics:
i) preferential localization and uptake by the immunoreactive cells;
ii) upon application of appropriate light intensities, killing those cells which have accumulated and retained the photosensiting agents;
iii) sparing of the normal hemopoietic stem cell compartment from the destructive effects of activated photosensitizers;
iv) potential utilization of photosensitizers for hematopoietic stem cell purging of immunoreactive cells in preparation for allogeneic or autologous stem cell transplantation; and
v) Potential utilization of photosensitizers for ex vivo elimination of reactive immune cells in patients with immunological disorders.

Therefore, in accordance with the present invention, there is provided a series of new rhodamine derivatives alone or in association with a pharmaceutically acceptable carrier; whereby photoactivation of said derivatives induces cell killing while unactivated derivatives of general structure represented by the formula (I), and salts thereof, are substantially non-toxic to cells.

In accordance with the present invention, there is also provided with the use of the photoactivable rhodamine derivatives according to the invention for the photodynamic treatment for the selective destruction and/or inactivation of immunologically reactive cells without affecting the normal cells and without causing systemic toxicity for the patient, wherein appropriate intracellular levels of said derivatives are achieved and irradiation of a suitable wavelength and intensity is applied.

In accordance with the present invention, there is also provided a method of prevention of graft-versus-host disease associated with allogeneic stem cell transplantation in a patient, which comprises the steps of:
a) activating lymphocytes from a donor by mixing donor cells with host cells for a time sufficient for a period of time sufficient for an immune reaction to occur,
b) substantially eliminating the activated lymphocytes of step a) with photodynamic therapy using a therapeutic amount of a photoactivable derivative or composition of claim 1 under irradiation of a suitable wavelength; and
c) performing allogenic stem cell transplantation using the treated mix of step b).

In accordance with the present invention, there is provided a method for the treatment of immunologic disorder in a patient, which comprises the steps of:
a) harvesting said patient's hematopoietic cells;
b) ex vivo treating of the hematopoietic cells of step a) by photodynamic therapy using a therapeutic amount of a photoactivable derivative or composition of claim 1 under irradiation of a suitable wavelength; and
c) performing graft infusion or autograft transplantation using the treated hematopoietic cells of step b).

The immunologic disorder may be selected from the group consisting of conditions in which self cells or donor cells react against host tissues or foreign targets, such as graft-versus-host disease, graft rejection, autoimmune disorders and T-cell mediated immunoallergies.

The hematopoietic cells may be selected from the group consisting of bone marrow, peripheral blood, and cord blood mononuclear cells.

For the purpose of the present invention the following terms are defined below.

The term "immunoreactive disorders" is intended to mean any alloimmune or autoimmune reaction and/or disorders.

In accordance with other aspects of the present invention, these rhodamine compounds which are prepared following the general strategy of halogenating known and readily available rhodamine dyes thereby generating a first and varied series of intermediates, which themselves can serve as potential photosensitizers or, use these halogenated rhodamines as intermediates in the synthesis of a second series of rhodamine dyes whereby one or more halogen has been substituted for one of the groups of structure (I). In the case where all of the halogens are replaced by new groups, a subsequent halogenation step is added to the sequence to obtain the desired compound of structure I (see FIGS. 1 to 5).

Testing of these compounds on various types of cells surprisingly revealed some of the candidate molecules to be non-toxic, more efficient and more selective than the known halogenated rhodamine dyes.

SUMMARY OF THE INVENTION

The present invention relates to rhodamine derivatives of the formula (I)

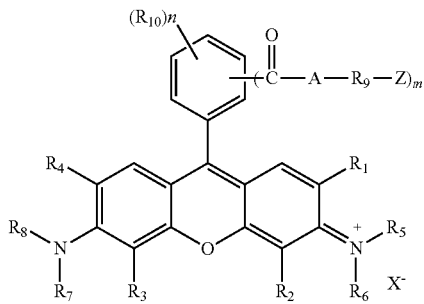

wherein:
one of $R_1$, $R_2$, $R_3$, $R_4$, and $R_{10}$ represents an halogen atom and each of the remaining $R_1$, $R_2$, $R_3$, $R_4$, and each of the remaining $R_{10}$ group is independently selected in the group constituted by hydrogen, halogen atoms, an amino, acylamino, dialkylamino, cycloalkylamino, azacycloalkyl, alkylcycloalkylamino, aroylamino, diarylamino, arylalkylamino, aralkylamino, alkylaralkylamino, arylaralkylamino, hydroxy, alkoxy, aryloxy, aralkyloxy, mercapto, alkylthio, arylthio, aralkylthio, carboxyl, alkoxycarbonyl, aryloxycarbonyl, aralkoxycarbonyl, carbamoyl, alkylcarbamoyl, dialkylcarbamoyl, cyano, hydroxysulfonyl, amidosulfonyl, dialkylamidosulfonyl, arylalkylamidosulfonyl, formyl, acyl, aroyl, alkyl, alkylene, alkenyl, aryl, aralkyl, vinyl, alkynyl group and by the corresponding substituted groups;
m=0-1;
n=1-4;
A is nil, O, or NH;
$R_9$ represents an alkylene group;
Z is H, amino, dialkylamino, or trialkylamino salt;
X is an anion; and
$R_5$, $R_6$, $R_7$, and $R_8$ are independently H or $C_1$-$C_6$ alkyl or $R_1$ in combination with $R_5$ or $R_6$, or $R_2$ in combination with $R_5$ or $R_6$, or $R_3$ in combination with $R_7$ or $R_8$, or $R_4$ in combination with $R_7$ or $R_8$ represents an alkylene, alone or in association with a pharmaceutically acceptable carrier.

The invention also relates to intermediates of the formula (II) to (VII) and to those of formula (I') as defined in 1 to 5, which are useful inter alia in the synthesis of the rhodamine derivatives of formula (I).

The invention further relates to the new processes for the synthesis of new rhodamines derivatives of formula (I), wherein the various groups $R_1$ to $R_{10}$, A, X, Y, Y' and Z, and m and n are as previously defined, without the exclusion of the compounds listed in the proviso at the end of the previous definition. This processes being defined by the schemes represented in FIGS. 1 to 5 and by the corresponding parts of the description.

The rhodamine derivatives of the invention are useful alone or in combination with a carrier, for treating infections generated by Gram+ and/or by Gram− bacteria. As well as in the treatment of diseases generated by enveloped viruses or by non-enveloped viruses.

Those compounds are also useful in the in-vivo and ex-vivo treatment of immunologic disorders.

BRIEF DESCRIPTION OF THE SCHEMES

FIG. 1 is the general synthesis of substituted 4 and 2,7 halogenated rhodamine derivatives.

FIG. 2 is the general synthesis of substituted 2 and 4,5 halogenated rhodamine derivatives.

FIG. 3 is the general synthesis of substituted 4- and 2,7-halogenated rhodamine derivatives.

FIG. 4 is the general synthesis of substituted 2- and 4,5-halogenated rhodamine derivatives.

FIG. 5 is the general synthesis of substituted 2- and 4,5-halogenated rhodamine derivatives.

FIG. 6 is the bacteriostatic activity of rhodamine derivatives against E. coli; the bacterial strain E. coli was treated with the rhodamine derivatives at 50 uM without extrusion time. The determined effects are expressed in log decrease of bacterial growth: HA-X-44: eradication; HA-X-164: 0.25 log; HA-X-171: 3.7 logs; HA-VIII-92: 6.2 logs; TH9402: 7 logs. LB is growth without compounds.

FIG. 7 is bacteriostatic activity of rhodamine derivatives against P. aeruginosa; the bacterial strain P. aeruginosa was treated with the rhodamine derivatives at 50 M without extrusion time. The determined effects are expressed in log decrease of bacterial growth: TH9402: 2 logs. LB is growth without compounds.

FIG. 8 is bacteriostatic activity of rhodamine derivatives against S. typhimurium; the bacterial strain S. typhimurium was treated with the rhodamine derivatives at 50 M without extrusion time. The determined effects are expressed in log decrease of bacterial growth: XA-X-44: 5 logs; HA-X-164; 0.3 log; TH9402: 6.7 logs. LB is growth without compounds.

FIG. 9 is bacteriostatic activity of rhodamine derivatives against P. aeruginosa; the bacterial strain P. aeruginosa was treated with the rhodamine derivatives at 50 μM without extrusion time. The determined effects are expressed in log decrease of bacterial growth: TH9402: 2 logs. LB is growth without compounds.

FIG. 10 is antiviral activity of rhodamine derivatives tested on cytomegalovirus; log decreases of viral infectivity and proliferation in FS cells. Compounds were added at 50 μM without extrusion time. Log decreases of viral infectivity and proliferation in FS cells: compounds were added at 50 μM without extrusion time and without light activation.

FIG. 11 is *staphilococcus epidermitis*; TH9402 inhibits bacterial growth of S. epidermitis at 50 μM without extrusion time.

FIG. 12 is *staphilococcus epidermitis*; HA-X-40 exhibits a bacteriostatic effect on the growth of S. epidermitis with a 2 logs decrease of bacterial growth at 50 IpM without extrusion time.

FIG. 13 is *staphilococcus epidermitis*; HA-X-40 eradicates bacterial growth of S. epidermitis at 50 μM with 90 minutes extrusion time.

FIG. 14 is, *staphilococcus epidermitis*; XA-X-44 eradicates bacterial growth of *S. epidermitis* at 50 µM without extrusion time.

FIG. 15 is *staphilococcus epidermitis*; HA-X-149 exhibits a bacteriostatic effect on the growth of *S. epidermitis* with a 4.5 logs decrease of bacterial growth at 50 M without extrusion time.

FIG. 16 is *staphilococcus epidermitis*; HA-X-164 exhibits a bacteriostatic effect on the growth of *S. epidermitis* with a 3 logs decrease of bacterial growth at 50 µM without extrusion time.

FIG. 17 is *staphilococcus epidermitis*; HA-X-171 exhibits a bacteriostatic effect on the growth of *S. epidermitis* with a 6.5 logs decrease of bacterial growth at 10 µM without extrusion time.

FIG. 18 is *staphilococcus epidermitis*; HA-VIII-92 exhibits a bacteriostatic effect on the growth of *S. epidermitis* with a 4 logs decrease of bacterial growth at 10 µM without extrusion time.

The following references mean:
HA-X-164: the acetate salt of 2,7-dibromorhodamine B methyl ester (4)
HA-X-149: the acetate salt of 2,7-dibromorhodamine B hexyl ester (8)
HA-X-171: 4,5-dibromorhodamine 6G (11)
HA-X-40: 2'-(6-dimethylamino-3-dimethylimino-3H-xanthen-9-yl) 4', 5'-dichloro-benzoic acid methyl ester hydrochloride (10)
HA-X-44: 4, 5-dibromorhodamine 110 2-(2-methoxy ethoxy) ethyl esther (13)
HA-VIII-92: rhodamine B 3-bromopropyl ester (14)
TH 9402: 4, 5-dibromorhodamine methyl ester 123.

DETAILED DESCRIPTION OF THE INVENTION

A first object of the present invention is constituted by the new rhodamines derivatives of the formula (I)

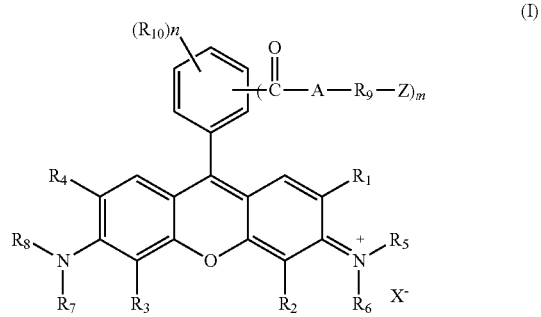

(I)

wherein: (0)
one of $R_1$, $R_2$, $R_3$, $R_4$, and $R_{10}$ represents an halogen atom and each of the remaining $R_1$, $R_2$, $R_3$, $R_4$, and each of the remaining $R_{10}$ group is independently selected in the group constituted by hydrogen, halogen atoms, an amino, acylamino, dialkylamino, cycloalkylamino, azacycloalkyl, alkylcycloalkylamino, aroylamino, diarylamino, arylalkylamino, aralkylamino, alkylaralkylamino, arylaralkylamino, hydroxy, alkoxy, aryloxy, aralkyloxy, mercapto, alkylthio, arylthio, aralkylthio, carboxyl, alkoxycarbonyl, aryloxycarbonyl, aralkoxycarbonyl, carbamoyl, alkylcarbamoyl, dialkylcarbamoyl, cyano, hydroxysulfonyl, amidosulfonyl, dialkylamidosulfonyl, arylalkylamidosulfonyl, formyl, acyl, aroyl, alkyl, alkylene, alkenyl, aryl, aralkyl, vinyl, alkynyl group and by the corresponding substituted groups;
m=0-1;
n=1-4
A is nil, O, or NH;
$R_9$ represents an alkylene group;
Z is H, amino, dialkylamino, or trialkylamino salt;
X is an anion; and
$R_5$, $R_6$, $R_7$, and $R_8$ are independently H or $C_1$-$C_6$ alkyl or $R_1$ in combination with $R_5$ or $R_6$, or $R_2$ in combination with $R_5$ or $R_6$, or $R_3$ in combination with $R_7$ or $R_8$, or $R_4$ in combination with $R_7$ or $R_8$ represents an alkylene, alone or in association with a pharmaceutically acceptable carrier,
with the proviso that the following specific compounds:
4,5-dibromorhodamine 123 (2-(4,5-dibromo-6-amino-3-imino-3H-xanthen-9-yl)-benzoic acid methyl ester hydrochloride) also called TH9402;
4,5-dibromorhodamine 123 (2-(4,5-dibromo-6-amino-3-imino-3H-xanthen-9-yl)-benzoic acid ethyl ester hydrochloride);
4,5-dibromorhodamine 123 (2-(4,5-dibromo-6-amino-3-imino-3H-xanthen-9-yl)-benzoic acid octyl ester hydrochloride);
4,5-dibromorhodamine 110 n-butyl ester (2-(4,5-dibromo-6-amino-3-imino-3H-xanthen-9-yl)-benzoic acid n-butyl ester hydrochloride); and
rhodamine B n-butyl ester (2-(6-ethyl amino-3-ethyl imino-3H-xanthen-9-yl)-benzoic acid n-butyl ester hydrochloride)
are excluded.

According to a preferred embodiment of this object of the invention
"alkyl" means a straight or branched aliphatic hydrocarbon group and the corresponding substituted alkyl group bearing one or more substituents which may be the same or different and which are selected in the group constituted by halo, aryl, hydroxy, alkoxy, aryloxy, alkyloxy, alkylthio, arylthio, aralkyloxy, aralkylthio, and cycloalkyl and "branched" means that a lower alkyl group such as methyl, ethyl or propyl is attached to a linear alkyl chain, preferred alkyl groups include the "lower alkyl" groups which are those alkyl groups having from about 1 to about 6 carbons., exemplary alkyl groups are methyl, ethyl, isopropyl, hexyl, cyclohexylmethyl, methyl or ethyl groups are more preferred;
"cycloalkyl" means a non-aromatic ring preferably composed from 4 to 10 carbon atoms, and the cyclic alkyl may be partially unsaturated, preferred cyclic alkyl rings include cyclopentyl, cyclohexyl, cycloheptyl, the cycloalkyl group may be optionally substituted with an aryl group substituent, the cyclopentyl and the cyclohexyl groups are preferred;
"alkenyl" means an alkyl group containing a carbon-carbon double bond and having preferably from 2 to 5 carbon atoms in the linear chain, exemplary groups include allyl vinyl;
"alkynyl" means an alkyl group containing a carbon-carbon triple bond and having preferably from 2 to 5 carbon atoms in the linear chain, exemplary groups include ethynyl, propargyl;
"acyl" means an aromatic carbocyclic radical or a substituted carbocyclic radical containing preferably from 6 to 10 carbon atoms, such as phenyl or naphthyl or phenyl or naphtyl substituted by at least one of the substituents selected in the group constituted by alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acylamino, aroylamino, carbamoyl, alkylcarbamoyl, dialkylcarbamoyl, alkylthio, arylthio, alkylene or —NYY' where Y and Y' are independently hydrogen, alkyl, aryl, or aralkyl;

"aralkyl" means a radical in which an aryl group is substituted for an alkyl H atom, exemplary aralkyl group is benzyl;

"acyl" means an alkyl-CO— group in which the alkyl group is as previously described, preferred acyl have an alkyl containing from 1 to 3 carbon atoms in the alkyl group, exemplary groups include acetyl, propanoyl, 2-methylpropanoyl, butanoyl or palmitoyl;

"aroyl" means an aryl-CO-group in which the aryl group is as previously described and preferably contains from 6 to 10 carbon atoms in the ring, exemplary groups include benzoyl and 1- and 2-naphtoyl;

"alkoxy" means an alkyl-O— group in which the alkyl group is as previously described, exemplary alkoxy groups include methoxy, ethoxy, n-propoxy, i-propoxy, n-butoxy, and heptoxy;

"aryloxy" means an aryl-O— group in which the aryl group is as previously described, exemplary aryloxy groups include phenoxy and naphthoxy;

"alkylthio" means an alkyl-S-group in which the alkyl group is as previously described, exemplary alkylthio groups include methylthio, ethylthio, i-propylthio and heptylthio;

"arylthio" means an aryl-S-group in which the aryl group is as previously described, exemplary arylthio groups include phenylthio, naphthylthio;

"aralkyloxy" means an aralkyl-O— group in which the aralkyl group is as previously described, exemplary aralkyloxy group is benzyloxy;

"aralkylthio" means an aralkyl-S— group in which the aralkyl group is as previously described, exemplary aralkylthio group is benzylthio;

"dialkylamino" means an —NYY' group wherein both Y and Y' are alkyl groups as previously described, exemplary alkylamino include ethylamino, dimethylamino and diethylamino;

"alkoxycarbonyl" means an alkyl-O—CO— group wherein the alkyl group is as previously described, exemplary alkoxycarbonyl groups include methoxy- and ethoxy-carbonyl;

"aryloxycarbonyl" means an aryl-O—CO— group wherein the aryl group is as previously described, exemplary aryloxycarbonyl groups include phenoxy- and naphthoxy-carbonyl;

"aralkoxycarbonyl" means an aralkyl-O—CO— group wherein the aralkyl is as previously defined, exemplary aralkoxycarbonyl group is benzyloxycarbonyl;

"carbamoyl" is an $H_2N$—CO-group;

"alkylcarbamoyl" is an Y'YN—CO— group wherein one of Y and Y' is hydrogen and the other of Y and Y' is alkyl as defined previously;

"dialkylcarbamoyl" is an Y'YN—CO— group wherein both Y and Y' are alkyl as defined previously;

"acylamino" is an acyl-NH group wherein acyl is as defined previously;

"aroylamino" is an aroyl-NH group wherein aroyl is as defined previously;

"akylene" means a straight or branched bivalent hydrocarbon chain group having preferably from 2 to 8 carbon atoms, and the alkylene group may be interrupted by one or more substituted nitrogen atoms wherein the substituent of the nitrogen atom is alkyl or oxygen or sulfur atoms, and it is presently more preferred that the alkylene group has from 2 to 3 carbon atoms, exemplary alkylene groups include ethylene (—$CH_2CH_2$—), propylene (—$CH_2CH_2CH_2$—), —$CH_2NMe\text{-}CH_2$—, O—$CH_2$—O or —O—$CH_2CH_2$—O—;

"halo" preferably means fluoro, chloro, bromo or iodo;

"azacycloalkyl" preferably means a 4 to 9 membered saturated carbon ring where one of the methylene groups is replaced by nitrogen;

"cycloalkylamine" means an —NYY' group wherein one of the Y and Y' is hydrogen and the other Y and Y' is cycloalkyl as defined previously;

"alkylcycloalkylamino" means an —NYY' group wherein one of the Y and Y' is alkyl as defined previously and the other Y and Y' is cycloalky as defined previously;

"diarylamino" means an —NYY' group wherein both Y and Y' are aryl groups as previously described;

"aralkylamino" means an —NYY' group wherein one of the Y and Y' is hydrogen and the other Y and Y' is aralkyl as defined previously;

"arylalkylamino" means an —NYY' group wherein one of the Y and Y' is alkyl as defined previously and the other Y and Y' is aryl as defined previously;

"alkylaralkylamino" means an —NYY' group wherein one of the Y and Y' is alkyl as defined previously and the other Y and Y' is aralkyl as defined previously;

"arylaralkylamino" means an —NYY' group wherein one of the Y and Y' is aryl as defined previously and the other Y and Y' is aralkyl as defined previously;

"mercapto" is a —SH or a SR group wherein R may be any of the above defined groups $R_1$ to $R_{10}$, the —SH, the mercaptoaryl and the mercaptoalkyl groups are preferred;

"hydroxysulfonyl" is an —$SO_3H$;

"amidosulfonyl" is an —$SO_2NH_2$;

"dialkylamidosulfonyl" means an —$SO_2NYY'$ group wherein both Y and Y' are alkyl groups as previously described;

"arylaralkylamidosulfonyl" means an —$SO_2NYY'$ group wherein one of the Y and Y' is aryl as defined previously and the other Y and Y' is aralkyl as defined previously; and "anion" means the deprotonated form of an organic or inorganic acid and the anion is preferably selected from hydrochlorides, hydrobromides, sulfates, nitrates, borates, phosphates, oxalates, tartrates, maleates, citrates, acetates, ascorbates, succinates, benzenesulfonates, methanesulfonates, cyclohexanesulfonates, toluenesulfonates, sulfamates, lactates, malonates, ethanesulfonates, cyclohexylsulfamates, and quinates. In the case where the rhodamine derivative bears one or more acidsubstituents, the covered compound comprise the internal salt or any salt derived from neutralization by any of the following bases: sodium hydroxide, potassium hydroxide, calcium hydroxide, lithium hydroxide, ammonia, ethylene diamine, lysine, diethanolamine, piperazine and the like.

A preferred embodiment of the invention is constituted by those rhodamine derivatives wherein at least 2 of the $R_1$, $R_2$, $R_3$, $R_4$, and $R_{10}$ groups represent an halogen atom which is preferably a bromide atom.

More preferred are those rhodamine derivatives, wherein the halogen(s) atom is(are) on the 2-7, 4-5 or 4'-5' position on the ring or is(are) at the end of the ester chain.

The following specific rhodamine derivatives are particularly interesting, the:

2'-(6-dimethylamino-3-dimethylimino-3H-xanthen-9-yl) 4',5'-dichloro-benzoic acid methyl ester hydrochloride;
4,5-dibromo rhodamine 110 2-(2-methoxy ethoxy) ethyl ester;
acetate salt of 2,7-dibromorhodamine B hexyl ester;
acetate salt of 2,7-dibromorhodamine B methyl ester;
4,5-dibromorhodamine 6G; and
rhodamine B 3-bromopropyl ester.

A second object of the present invention is constituted by the intermediates represented by the formulae (II) to (VII) and (I'), the formulae being as defined in FIGS. 1 to 5, wherein the various groups are as previously defined without any disclaimer. The intermediates being as defined in FIGS. 1 to 5.

A third object of the present invention is constituted by new processes for the synthesis of new rhodamines derivatives of formula (I) wherein the various groups $R_1$ to $R_{10}$, A, X, Y, Y' and Z, and m and n are as previously defined, without the exclusion of the compounds listed in the proviso at the end of the previous definition. These processes being defined by the schemes represented in FIGS. 1 to 5 and by the corresponding parts of the description.

A fourth object of the present invention is constituted by the use of at least one rhodamine derivatives as defined in the first object of the invention, without the exclusion of the compounds listed in the proviso at the end of definition of the rhodamine derivative of formula (I), alone or in combination with a carrier, for treating infections generated by Gram+ and/or by Gram− bacteria.

According to a preferred embodiment of the present invention the rhodamine derivatives are use for treating infections generated by *Staphylococcus* epidermitis.

Particularly interesting are:
the use of the 4,5-dibromo rhodamine 110 2-(2-methoxy ethoxy) ethyl ester as bacteriostatic agent against *Escherichia coli* 0157:H7 and/or against *Salmonella* thyphimurium LT2;
the use of the acetate salt of 2,7-dibromorhodamine B hexyl ester as bacteriostatic agent against *Salmonella thyphimurium* LT2;
the use of the 4,5-dibromorhodamine 6G as bacteriostatic agent against *Escherichia coli* 0157:H7;
the use of the rhodamine B 3-bromopropyl ester as bacteriostatic agent against *Escherichia coli* 0157:H7; and
the use of the 4,5-dibromorhodamine methyl ester as bacteriostatic agent against *Escherichia coli* 0157:H7, *Salmonella thyphimurium* LT2 and/or *Pseudomonas aeruginosa*.

Preferably for this therapeutical use the rhodamine(s) derivative(s) is (are) combined with a carrier that is a pharmaceutically acceptable carrier and is preferably selected in the group constituted by 5% mannitol and/or DMSO.

Any carrier is possible, however, the acceptable carrier is preferably constituted by 5% of mannitol: in water or in DMSO.

In the case of acetate salt of 2,7-dibromorhodamine B hexyl ester, of the HA-X-149, of the HA-X-164, the carrier is preferably constituted by DMSO.

A fifth object of the present invention is constituted by a bactericidal composition for the treatment of a liquid contaminated with Gram+ and/or Gram− bacteria, which composition comprises an effective amount of at least one rhodamine derivatives as above defined, without the exclusion of the compounds listed in the proviso at the end of claim 1, alone or in combination with a carrier.

A sixth object of the present invention is constituted by a bactericidal solution, for the treatment of a locus contaminated with Gram+ and/or Gram− bacteria, which solution comprises an effective amount of at least one rhodamine derivatives of formula (I) as previously defined, without any disclaimer, alone or in combination with a carrier for treating infections generated by Gram+ and/or Gram− bacteria.

A seventh object of the present invention is constituted by a method for treating infections generated by Gram+ and/or Gram− bacteria, which method comprises administering to a human or animal in need an effective amount of at least one rhodamine derivatives of formula (I) as previously defined, without any disclaimer, alone or in combination with a carrier.

According to a preferred embodiment of this method, the effective amount administered is comprises between 0.5 and 200 mg per kilogram body weight per day.

A eight embodiment of the present invention is constituted by a medicament containing an effective amount of at least one rhodamine derivatives of formula (I) as previously defined, without the exclusion of the compounds listed in the proviso at the end of the definition, alone or in combination with a carrier, for treating infections generated by Gram+ and/or Gram− bacteria.

A tenth object of the present invention is constituted by the use of an effective amount of at least one rhodamine derivatives or salt thereof as above-defined without any disclaimer, alone or in combination with a carrier, in the treatment of diseases generated by enveloped viruses or by non-enveloped viruses.

Preferably, the enveloped virus is one with a double stranded ADN, more preferably one of the Herpes viridae family.

An eleventh object of the present invention is constituted by medicament containing an effective amount of at least one rhodamine derivatives or salt thereof, as above, without the exclusion of the compounds listed at the end of the definition of the rhodamine derivatives of formula (I), alone or in combination with a carrier, for treating viral infections.

Further preferred embodiment of the present invention are the use of:
the 4,5-dibromo rhodamine 2'-(6-dimethylamino-3-dimethylimino-3H-xanthen-9-yl)-4', 5'-dichloro benzoic acid methyl ester hydrochloride;
4,5-dibromo rhodamine 110 2-(2-methoxy ethoxy) ethyl as an antiviral agent against cytomegalovirus;
4,5-dibromorhodamine methyl ester as an antiviral agent against cytomegalovirus; and
the acetate salt of 2,7-dibromorhodamine B hexyl ester as an antiviral agent against Cytomegalovirus.

Another preferred embodiment of the invention is constituted by the 2,7-dibromorhodamine B hexyl ester acetate salt as an antiviral agent against Cytomegalovirus.

Use of the acetate salt of 2,7-dibromorhodamine B hexyl ester as an antiviral agent against Cytomegalovirus A twelfth object of the present invention is the use of the rhodamine derivatives of formula (I) as previously defined, without any disclaimer, in the treatment of immunologic disorders.

According to a preferred embodiment, the use relates to enhancing high quantum-yield production and singlet oxygen generation upon irradiation while maintaining desirable differential retention of rhodamine between normal and cancer cells, said rhodamine derivatives of formula (I) being as previously defined, without the disclaimer.

According to another embodiment, the use relates to the photodynamic therapy of cancer patients by destroying human cancer cells, wherein appropriate intracellular levels of said derivatives are achieved and irradiation of a suitable wavelength and intensity is applied.

According to a further preferred embodiment, the use of the invention relates to a method for the photodynamic therapy of patients suffering from leukemias, disseminated multiple myelomas or lymphomas, which comprises the steps of:
a) harvesting said patient's human bone marrow;
b) purging of the bone marrow of step a) by photodynamic therapy using a therapeutic amount of a photoactivable derivative according to formula (I), without the exclusion of the compounds listed in the proviso at the end of the definition, under irradiation of a suitable wavelength; and
c) performing autologous stem cell transplantation using the purged bone marrow of step b).

Preferably, the purging of step b) further comprises intensive chemotherapy and total body irradiation (TBI) procedures.

Another preferred embodiment relates to a method for in vitro purging of the human bone marrow containing metastasis of solid tumors, selected from the group consisting of metastasis of breast, lung, prostatic, pancreatic and colonic carcinomas, disseminated melanomas and sarcomas, wherein surgical excision or debulking can be achieved, which comprises the steps of:
a) harvesting said patient's human bone marrow;
b) purging of the bone marrow of step a) by photodynamic therapy using a therapeutic amount of at least one photoactivable derivative of formula (I) as above defined without any disclaimer, under irradiation of a suitable wavelength; and
c) performing autologous stem cell transplantation using the purged bone marrow of step b).

Preferably, the purging of step b) further comprises intensive chemotherapy and total body irradiation (TBI) procedures.

A further embodiment of this object of the invention is a method for the photodynamic therapy of cancer patients, which comprises administering to said patients a therapeutically acceptable intracellular level of at least one photoactivable derivative of formula (I) as above defined, without disclaimer, and subjecting said patients to irradiation of a therapeutically suitable wavelength.

Preferably, at least one photoactivable derivative is administered by instillation, injection, bloodstream diffusion at the tumor sites directly accessible to light emission or tumor sites accessible to laser beams using rigid or flexible endoscopes.

More preferably, the laser-accessible tumor site is selected from the group consisting of urinary bladder, oral cavity, esophagus, stomach, lower digestive tract, upper and lower respiratory tract.

Another preferred embodiment of this object of the invention is constituted by a method for the treatment of leukemias in patients, which comprises the steps of:
a) purging of cancerous clones from the bone marrow of said patients;
b) subjecting said purged clones of step a) to a photodynamic treatment using a therapeutical amount of at least one of the photoactivable derivatives of formula (I) as previously defined, without the disclaimer present at the end of the definition, under irradiation of a suitable wavelength for the selective destruction of leukemic cells without affecting the normal cells of the patients; and
c) administering said treated clones of step b) to the patients; thereby causing no systemic toxicity for the patients.

A fourteenth object of the present invention is constituted by a photoactivable pharmaceutical composition for the selective destruction and/or inactivation of immunologically reactive cells without affecting the normal cells and without causing systemic toxicity for the patient, said composition comprising at least one photoactivable rhodamine derivative of formula (I) as previously defined, without the exclusion of the compounds listed in the proviso at the end of the definition, and photoactivable derivatives thereof; in association with a pharmaceutically acceptable carrier; whereby photoactivation of said derivatives induces cell killing while inactivated derivatives are substantially non-toxic to cells.

A fifteenth object of the present invention is constituted by the use of the photoactivable derivatives of claim 1 for the photodynamic treatment for the selective destruction and/or inactivation of immunologically reactive cells without affecting the normal cells and without causing systemic toxicity for the patient, wherein appropriate intracellular levels of said derivatives are achieved and irradiation of a suitable wavelength and intensity is applied.

A preferred embodiment is constituted by a method of prevention of graft-versus-host disease associated with allogeneic stem cell transplantation in a patient, which comprises the steps of:
a) activating lymphocytes from a donor by mixing donor cells with host cells for a time sufficient for a period of time sufficient for an immune reaction to occur;
b) substantially eliminating the activated lymphocytes of step a) with photodynamic therapy using a therapeutic amount of a photoactivable composition of claim 24 under irradiation of a suitable wavelength; and
c) performing allogenic stem cell transplantation using the treated mix of step b).

Another preferred embodiment is constituted by a method for the treatment of immunologic disorder in a patient, which comprises the steps of:
a) harvesting said patient's hematopoietic cells;
b) ex vivo treating of the hematopoietic cells of step a) by photodynamic therapy using a therapeutic amount of a photoactivable composition of claim 24 under irradiation of a suitable wavelength; and
c) performing graft infusion or autograft transplantation using the treated hematopoietic cells of step b).

Preferably, the immunologic disorder is selected from the group consisting of conditions in which self cells or donor cells react against host tissues or foreign targets, such as graft-versus-host disease, graft rejection, autoimmune disorders and T-cell mediated immunoallergies.

More preferably, the hematopoietic cells is selected from the group consisting of bone marrow, peripheral blood, and cord blood mononuclear cells.

Compounds of structure I exhibit enhanced properties as: labeling dyes for deoxynucleotides, dideoxynucleotides and polynucleotides; novel dyes suitable for recording fluids for the ink jet process; novel dyes for fiberglass and paper; novel dyes for the eradication of infectious biological contaminants in body tissues; novel dyes applicable in photographic processes; novel dyes applicable in cancer chemotherapy; novel dyes applicable as inhibitors of the herpes simplex virus thymidine kinase and in the treatment and/or in the prophylaxis of infections caused the herpes simplex virus; novel dyes for use as polymer optical amplifiers and lasers; novel dyes applicable in cell biology; novel dyes applicable in the doping of siliceous materials to give solid dye lasers; novel pigments applicable for paints, inks and plastics; novel organic reagents in solvent extraction of metal ions; novel dyes applicable in the formation of new conjugate products with other dyes; novel dyes for the manufacture of CD-ROM type optical memory disks; novel dyes applicable in the fluorophore labeling of peptides; novel dyes applicable in the flow cytometry analysis; novel dyes applicable as stains for the detection of *Mycobacterium tuberculosis* by fluorescence microscopy; novel dyes applicable in the fluorescent mapping of binding sites for substrates, ligands and inhibitors, novel dyes to study transport through the blood-brain-barrier; novel dyes to study biofilm desinfection; novel dyes applicable as fluorescent probes in cell biology; novel dyes for use as water tracing; novel dyes for visualization of peptide receptors by image intensified fluorescence microscopy; novel dyes for the formation of metal chelates in analytical chemistry; novel fluorescent dyes applicable in diagnosis therapy.

Chemical Synthesis

These compounds are prepared following the general strategy of halogenating known and readily available rhodamine dyes thereby generating a first and varied series of intermediates, which themselves can serve as potential photosensitizers or, use these halogenated rhodamines as intermediates in the synthesis of a second series of rhodamine dyes whereby one or more halogen has been substituted for one of the groups of structure I. In the case where all of the halogens are replaced by new groups, a subsequent halogenation step is added to the sequence to obtain the desired compound of structure I, (see the illustrative schemes I and 2).

Due to the specific retention of the rhodamine 123 class of dyes by the abnormal malignant cells and the concomitant lack of their accumulation by the normal hematopoietic stem cells, these results provide evidence for the potential use of these three new dyes for in vivo or in vitro photodynamic therapy.

In accordance with the present invention, there is provided the use of such above-mentioned dyes in conjugation with tumor specific antibodies, or poisonous substances, or liposomal or lipoproteins, or fluorochrome adducts.

In addition, the photosensitizers to be described have the potential to act synergistically in conjunction with other photoactive substances.

Moreover, the negative selection procedure provided by the use of photodynamic treatment does not preclude the use of other means for enriching hematopoietic stem cells such as positive selection with anti-CD34 monoclonal antibodies.

Other Clinical Applications

In addition to using photosensitizers in the context of in vitro bone marrow purging for the leukemias and metastatic cancers, the molecules can also be used in vivo for tumor sites directly accessible to exposure to a light source and to appropriate local concentrations of the drugs to be described. The molecules of the invention can also be utilized in the photodynamic therapy of a patient suffering from disseminated multiple myelomas or lymphomas. The metastatic cancers for which the therapy of this invention is appropriate include metastasis of breast, lung, prostatic, pancreatic and colonic carcinomas, disseminated melanomas and sarcomas. The photoactivable derivatives of the present invention can be administered by instillation, injection, bloodstream diffusion at the tumor sites directly accessible to light emission of tumor sites accessible to laser beams using rigid or flexible endoscopes.

DESCRIPTION OF PREFERRED EMBODIMENTS

As a matter of illustration only, 5 methods of treatment of immunologic disorders involving the rhodamine derivatives according to the invention are thereafter illustrated.

Method I of Treatment of Leukemias

1. Diagnostic Procedures

Diagnosis of chronic myelogenous leukemia (CML) will be established using one or more of the following procedures on blood or bone marrow cells:
  a) conventional cytogenetics studies with identification of Ph 1+ metaphases harbouring the t(9:22);
  b) fluorescent in situ hybridization for the detection of the bcr/abl rearrangement; and
  c) Southern blot analysis for the detection of a rearranged her fragment or PCR-RT for the detection of chimeric ber/abl messenger RNA.

2. Bone Marrow Harvesting

After diagnosis, bone marrow (BM) or peripheral blood (PB) derived hemopoietic stem cells will be harvested using previously described procedures for the autologous marrow transplantation in cancer therapy (reviewed by Herzig G P, (1981) *Prog. Hematol.,* 12:1). Hemopoietic stem cells collected for autograft will be immediately treated ex vivo as described below.

3. In Vitro Purging of Leukemia

Ex vivo treatment consists, of short-term incubation or BM of PB stem cells with one or several of the selected photoactive compounds. Duration of incubation, cell concentration and drug molarity are be determined for each patient using an aliquot of the harvested cell population. Excess of dyes will be removed by cell washes with sterile dye free medium supplemented with 2% autologous serum. Cells are next exposed to radiant energy of sufficient intensities to effect photodynamic purging of leukemia cells. Efficacy of the photodynamic purging procedure is verified on an aliquot of the treated cell population, before cryopreservation and/or re-infusion to the patient is performed. Until re-infusion to the patient, the cells are cryopreserved in 10% dimethyl sulfoxyde (DMSO)—90% autologous serum medium, at −196° C. in the vapour phase of liquid nitrogen.

4. Systemic Treatment of Patients

Following stem cell harvest, patient will be either treated with conventional regimens until autografting is clinically indicated or immediately submitted to dose-intensive chemotherapy and total body irradiation where indicated.

5. Autologous Stem Cell Transplantation

Following appropriate treatment of the patient by high-dose chemotherapy and irradiation and at the appropriate clinical moment, cryopreserved marrow or peripheral blood stem cells will be rapidly thawed and diluted in medium containing 25 UI DNase $ml^{-1}$ to minimize clumping. A minimum of $2\times10^7$/kg nucleated cells with 85% to 95% viability as measured by Trypan™ blue exclusion will be returned to the patient.

Method II of Treatment of Malignancies

1. Diagnostic Procedures

Diagnosis of malignancies will be established using conventional histopathological examination of the primary tumor. Detection of marrow involvement by neoplastic cells will be achieved by direct histological examination and ancillary procedures where indicated (i.e. immuno-peroxydase, immunohistochemical, tumor markers and hybridization studies).

2. Bone Marrow Harvesting

After diagnosis, bone marrow (BM) or peripheral blood (PB) derived hemopoietic stem cells will be harvested using previously described procedures for the autologous marrow transplantation in cancer therapy (reviewed by Herzig G P, (1981) *Prog. Hematol.*, 12:1). Hemopoietic stem cells collected for autograft will be treated immediately ex vivo as described below.

3. In Vitro Purging of Leukemia

Ex vivo treatment will consist of short-term incubation of BM of PB stem cells with one or several of the selected photoactive compounds. Duration of incubation, cell concentration and drug molarity will be determined for each patient using an aliquot of the harvested cell population. Excess of dyes will be removed by cell washes in sterile dye free medium supplemented with 2% autologous serum. Cells will next be exposed to radiant energy of sufficient intensities to effect photodynamic purging of leukemia cells. Whenever a sensitive molecular marker is available, an aliquot of the treated cell population will be tested for the detection of residual neoplastic cells before cryopreservation and/or re-infusion to the patient is attempted. The cells will be cryopreserved in 10% dimethyl sulfoxyde (DMSO)—90% autologous serum medium, at 196° C. in the vapour phase of liquid nitrogen.

4. Systemic Treatment of Patients

Following stem cell harvest, patient will be either treated with conventional regimens until autografting is clinically indicated or immediately submitted to dose-intensive chemotherapy and total body irradiation where indicated.

5. Autologous Stem Cell Transplantation

Following high-dose chemotherapy and irradiation cryopreserved marrow or peripheral blood stem cells will be rapidly thawed and diluted in medium containing 25 UI DNase $Ml^{-1}$ to minimize clumping. A minimum of $2 \times 10^7$/kg nucleated cells with 85% to 95% viability as measured by Trypan™ blue exclusion will be returned to the patient.

Method III of Prevention of Graft-Versus-Host Disease in the Context of Allogeneic Stem Cell Transplantation 1. Diagnosis and Identification of Immunological Differences Between Donor and Recipient, and Graft-Versus-Host Disease:

Allogeneic stem cell transplantation is performed for numerous neoplastic and non-neoplastic conditions. Hematological malignancies are comprised of leukemia, lymphoma, multiple myeloma, myelodysplastic syndromes, etc.; and non-hematological malignancies: aplastic anemia, congenital disorders, severe immunodeficiency syndromes, rhumatoid arthritis, scleroderma, lupus erythematosus, multiple sclerosis, and other immune disorders.

Graft-versus-host disease is a complication of allogeneic stem cell transplantation, where donor cells react against host cells, damaging target tissues (usually skin, liver, gut, lung, lacrymal or salivary glands, etc.). The diagnosis relies on several clinical and laboratory parameters, that are extensively reviewed in *Graft-vs.-Host Disease*, Ferrara J L M, Deeg H J, Burakoff S J eds, Marcel Dekker, New York, 1997.

GVHD develops against antigens present on recipient cells but not on donor cells. Immunological differences between donor and recipient could be present at the level of major histocompatibility antigens, minor histocompatibility antigens or tumor-associated antigens. Disparity will be established using one or more of the following procedures on blood or bone marrow cells:

a) HLA typing: conventional serologic typing or molecular to identify disparities between donor and recipient in major histocompatibility complex class I and class II antigens; and b) Mixed lymphocyte culture to identify differences in class II antigens; and c) Minor histocompatibility antigens: although a few cytotoxic T cell lines are available and could be used to identify minor histocompatibility antigens, currently, these tests are only available for research purposes.

2. Progenitor Cell Harvesting

After diagnosis, bone marrow (BM) or peripheral blood (PB) or cord-blood derived hemopoietic stem cells from the donor will be harvested using previously described procedures for allogeneic progenitor cell transplantation (reviewed in Bone Marrow Transplantation, Forman S J, Blume K G, Thomas E D eds, Blackwell Scientific Publications, Cambridge Mass., USA, 1994). Donor hemopoietic stem cells collected for allografting will be immediately incubated with irradiated (25Gy) host mononuclear or other cells. Host cells admixed with donor cells are incubated in sterile dye free medium supplemented with 20% autologous serum and interleukin-2 for 2 days. This procedure elicits donor cell alloreactivity towards the host, and the cell graft subsequently undergoes photodynamic treatment ex vivo as described below.

3. Selective In Vitro Purging of Immunoreactive Cells

Ex vivo treatment will consist of short-term incubation of previously activated BM or PB stem cells with one or several of the selected photoactive compounds. Duration of incubation, cell concentration and drug molarity will be determined for each patient using an aliquot of the harvested cell population. Excess of dyes will be removed by cell washes with sterile dye free medium supplemented with 2% autologous serum. Cells will next be exposed to radiant energy of sufficient intensities to effect photodynamic purging of leukemia cells. Efficacy of the photodynamic purging procedure will be verified on an aliquot of the treated cell population, before cryopreservation and/or re-infusion to the patient is performed. Until re-infusion to the patient, the cells will be cryopreserved in 10% dimethylsulfoxyde (DMSO)—90% autologous serum medium, at −196° C. in the vapor phase of liquid nitrogen.

4. Systemic Treatment of Patients

Following stem cell harvest, the patient will be submitted to dose-intensive chemotherapy and/or irradiation when indicated.

5. Allogeneic Stem Cell Transplantation

Following appropriate treatment of the patient by high-dose chemotherapy and/or irradiation and at the appropriate clinical moment, cryopreserved marrow or peripheral blood or cord blood stem cells will be rapidly thawed and returned to the patient.

Method IV of Treatment of Graft-Versus-Host Disease and Autoimmune Diseases

1. Diagnostic Procedures

Diagnosis of graft-versus-host disease or immunoreactive disorders will be established using conventional clinical, biochemical and/or histopathological examination of the blood or appropriate tissues. Diagnostic and predictive features of GVHD are reviewed in *Graft-vs.-Host Disease*, Ferrara J L M, Deeg H J, Burakoff S J eds, Marcel Dekker, New York, 1997.

2. Harvesting of Peripheral Blood Cells

After diagnosis of severe GVHD, autoimmune or immunoreactive disorder, peripheral blood (PB) mononuclear cells will be harvested using previously described or similar leukopheresis procedures (reviewed in *Bone Marrow Transplantation*, Forman S J, Blume K G, Thomas E D eds, Blackwell Scientific Publications, Cambridge Mass., USA, 1994). Patient's peripheral blood mononuclear cells collected will be treated immediately ex vivo as described below.

3. In Vitro Elimination of Cells Mediating GVHD

Ex vivo treatment will consist of short-term incubation of PB stem cells with one or several of the selected photoactive compounds. Duration of incubation, cell concentration and drug molarity will be determined for each patient using an aliquot of the harvested cell population. Excess of dyes will be removed by cell washes in sterile dye free medium supplemented with 2% autologous serum. Cells will next be exposed to radiant energy of sufficient intensities to effect photodynamic purging of activated cells, which mediate GVHD.

4. Administration of Photodynamically Treated Cells to Patients

Leukopheresed cells that are photodynamically treated will be reinfused into the patient. This approach will enable the elimination of a large number of circulating activated lymphocytes and other cells involved in GVHD. In addition, cells spared by the photodynamic treatment are unactivated and their reinfusion into the patient may help restore normal immunologic equilibrium.

Method V of Treatment of Immunologic Disorders

1. Diagnostic Procedures

Diagnosis of autoimmune disorders will be established using conventional clinical, biochemical and/or histopathological examination of the blood or appropriate tissues. Severe autoimmune diseases are amenable to autologous transplantation (reviewed in Sullivan K M et al., *Am. Soc. Hematol.*, Educ. Program Book, 1998: 198-214).

2. Harvesting of Hematopoietic Stem Cells

After diagnosis, bone marrow (BM), peripheral blood (PB) or cord blood (CB) mononuclear cells will be harvested using previously described procedures for the autologous marrow transplantation in cancer therapy (reviewed in Bone Marrow Transplantation, Forman S J, Blume K G, Thomas E D eds, Blackwell Scientific Publications, Cambridge Mass., USA, 1994). Patient's hemopoietic stem cells collected for autograft will be treated immediately ex vivo as described below.

3. In Vitro Elimination of Cells Mediating Autoimmune Disorders

Ex vivo treatment will consist of short-term incubation of BM or PB stem cells with one or several of the selected photoactive compounds. Duration of incubation, cell concentration and drug molarity will be determined for each patient using an aliquot of the harvested cell population. Excess of dyes will be removed by cell washes in sterile dye free medium supplemented with 2% autologous serum. Cells will next be exposed to radiant energy of sufficient intensities to effect photodynamic purging of immunoreactive cells, which mediate the immunologic disorder.

4. Administration of Photodynamically Treated Cells to Patients

Hematopoietic stem cells that are photodynamically treated will be stored (frozen or kept in culture). This approach will enable the elimination of a large number of activated lymphocytes and other cells involved in the immunologic disorder. In addition, cells spared by the photodynamic treatment are unactivated and their reinfusion may help restore normal immunologic equilibrium. Following stem cell harvest, patient will be either treated with conventional regimens until autografting is clinically indicated or immediately submitted to dose-intensive chemotherapy and total body irradiation where indicated.

5. Autologous Stem Cell Transplantation

Following high-dose chemotherapy and irradiation cryopreserved marrow or peripheral blood stem cells will be rapidly thawed and infused to the patient.

The preparation of those rhodamine derivatives of formula (I), as above defined, without the proviso, will be more readily understood by referring to the following examples which are given for illustrative purpose.

I Synthesis of 2,7-Dibromorhodamine B Methyl Ester Acetate Salt (4)

I-1 Preparation of Rhodamine B Methyl Ester (1)

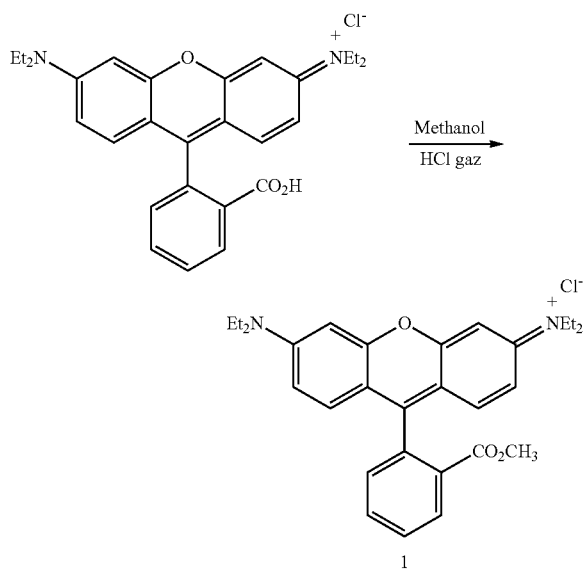

To a stirred mixture of 1.63 g (3.40 mmol) of Rhodamine B and 100 ml of methanol, hydrochloric acid was bubbled through the solution for 45 min and the reaction mixture was refluxed overnight. The methanol was evaporated under reduced pressure and the dark red residue was then purified by flash chromatography using a mixture of methanol and dichloromethane (1:9) as eluent to afford the desired product as a deep red viscous residue (1.54 g).

Rf: 0.52 (MeOH: CH$_2$Cl$_2$ 1.5: 8.5)
Yield: 92%
Ms (FAB): Calculated for C$_{29}$H$_{33}$O$_3$N$_2$: (M-Cl)$^+$: 457.2491
Found (M-Cl)$^+$: 457.2494
UV(MeOH): $\lambda_{max}$ 555 nm I-2 Preparation of Dihydrorhodamine B Methyl Ester (2)

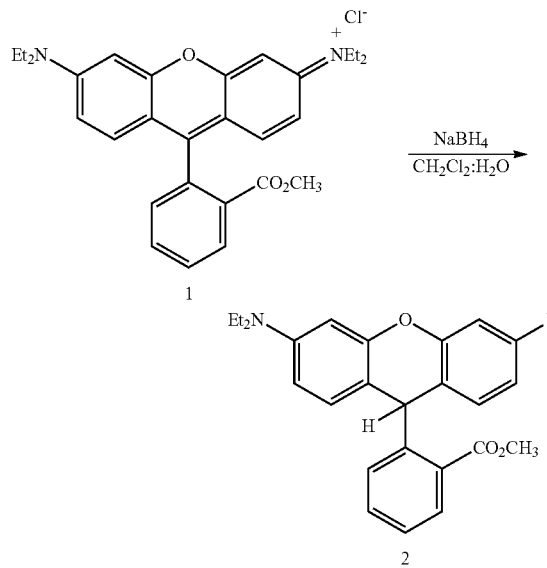

Rhodamine B methyl ester 1.73 g (3.50 mmol) was dissolved in 250 ml of dichromethane and 100 ml of water. Excess NaBH$_4$ (solid) was added in portion with vigorous stirring, during 30 min, until the initial dark red colour was discharged. The pale orange organic phase was separated and the aqueous phase extracted twice with dicholoromethane. The combined organic layers were dried on Na$_2$SO$_4$, filtered and evaporated under reduced pressure and the residue purified by flash chromatography using ethyl acetate as the eluting solvent. Fractions containing the product were combined and the solvent evaporated to afford the product 2 as a pink oil (1.50 g).
Rf: 0.84 (AcOEt)
Yield: 93.7%

I-3 Bromination of Dihydrorhodamine B Methyl Ester (2)

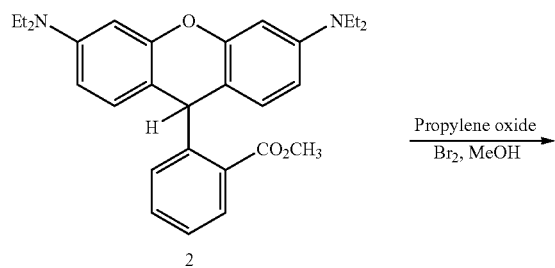

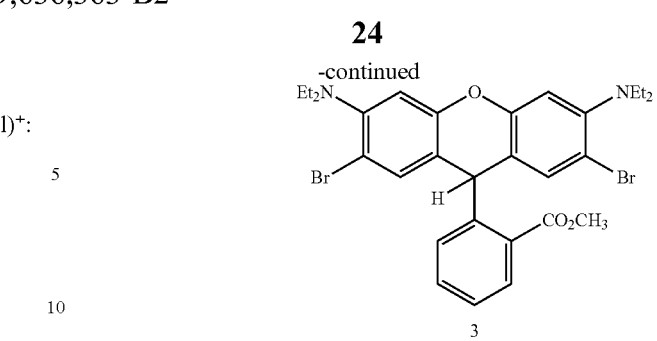

In a 250 ml round bottom flask we introduced dihydrorhodamine B methyl ester (2) 1.34 g (2.92 mmol) and 112 ml of methanol spectrograde. The mixture was stirred at room temperature until all the ester was dissolved. Propylene oxide 2 eq. (409 μL, 5.85 mmol) was added followed by dropwise addition of bromine 2 eq. (300 μL, 5.85 mmol). The stirring was continued at room temperature for 1 h 30 min. The volatile solvent were evaporated under reduced pressure and the red oily residue was subjected to purification by flash chromatography using ethyl acetate and hexanes (0.5: 9.5) as eluent to give the desired compound 3 as foam white solid (570 mg)
Rf: 0.41 (AcOEt: Hexanes 0.5: 9.5)
Yield: 31.6%
Nmr: (CD$_3$OD) δ 7.86 (dd, J=1.44 and 7.8 Hz, 1H); 7.44 (m, 1H); 7.32 (m, 1H); 7.16 (s, 2H); 7.10 (dd, J=1.45 and 7.8 Hz, 1H); 6.93 (s, 2H); 6.17 (s, 1H); 3.94 (s, 3H); 3.09 (q, J=7.09 Hz, 8H); 1.04 (t, J=7.09 Hz, 12H).
Ms (FAB): (MH)$^+$ 615.1

I-4 Oxydation of the 2,7-dibromodlhydrorhodamine B Methyl Ester and Formation of the Acetate Salt of 2,7-dibromorhodamine B Methyl Ester (4)

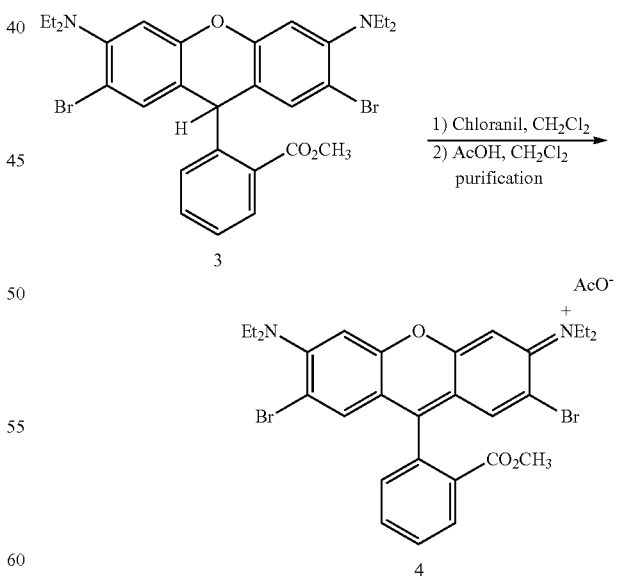

To a stirred solution of 2,7-dibromodihydrorhodamine B methyl ester (3) 400 mg (0.64 mmol) in 10 ml of dichloromethane was added chloranil (1.2 eq., 0.77 mmol, 192 mg). The reaction mixture was stirred at room temperature overnight, then the reaction was stopped and the solvent was evaporated under reduced pressure to give a purple residue. The oxidized compound obtained in the precedent step was dissolved in 15 ml of dichloromethane and acetic acid (0.8 ml) was added dropwise. The clear red solution obtained was stirred for 5 min, at room temperature, followed by the evaporation of the volatile solvent under reduced pressure to give a purple viscous residue. The residue was purified by flash chromatography using a 10% methanol in dichloromethane as eluent to give the desired compound 4 as a viscous purple solid (200 mg).

Rf: 0.29 (MeOH: $CH_2Cl_2$ 1:9)

Yield: 45.7%

Nmr: ($CD_3OD$) δ 8.48 (dd, J=1.45 and 7.5 Hz, I H); 7.95 (m, 2H); 7.52 (dd, J=1.6 and 7.2 Hz, 1H); 7.45 (s, 2H); 7.38 (s, 2H); 3.79 (q, J=8 Hz, 81-1); 3.71 (s, 3H); 1.99 (s, 3H); 1.37 (t, J=7.02 Hz, 2H)

Ms (FAB): Calculated for $C_{29}H_{32}O_3N_2Br_2$ (MH-AcO)$^+$ 614.0779

Found: 614.0765

UV (MeOH): $\lambda_{max}$ 577 nm

Example II

II Synthesis of 2,7-dibromorhodamine B Hexyl Ester Acetate Salt (8)

II-1 Preparation of Rhodamine B Hexyl Ester (5)

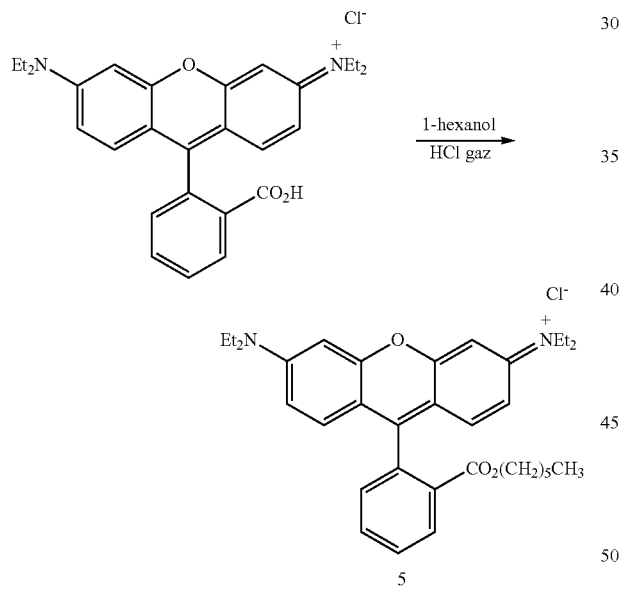

To a stirred mixture of 2.39 g (4.98 mmol) of Rhodamine B and 120 ml of 1-hexanol, hydrochloric acid was bubbled through the solution for 45 min and the reaction mixture was refluxed overnight. The I-hexanol was then distilled under reduced pressure and the dark red residue was purified by flash chromatography using a mixture of methanol and dichloromethane (1:9) as eluent. After the evaporation of the volatile solvents we obtained a viscous red green residue (2.62 g).

Rf: 0.45 (MeOH: $CH_2Cl_2$ 1.2:8.8)

Yield: 93.5%

Ms (FAB): Calculated $C_{34}H_{43}O_3N_2$ (M-Cl)$^+$: 527.3273

Found: 527.3261

UV (MeOH): $\lambda_{max}$ 555 nm

II-2 Preparation of Dihydrorhodamine B Hexyl Ester (6)

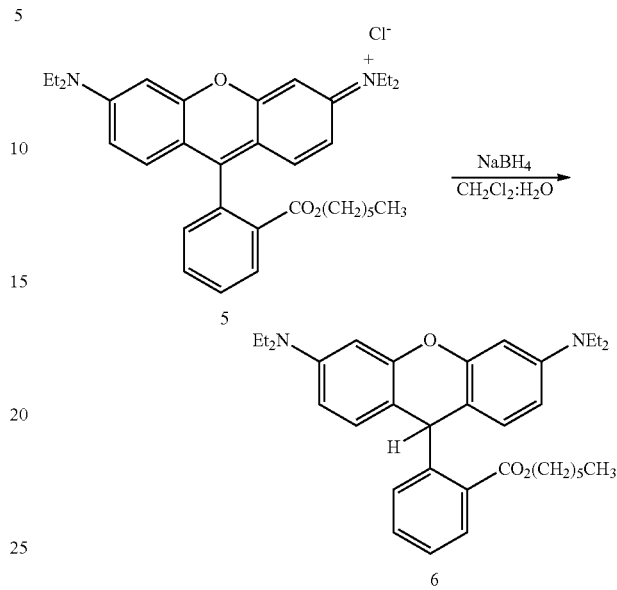

Rhodamine B hexyl ester (5) 940 mg (1.66 mmol) was dissolved in 200 ml of dichromethane and 150 ml of water. Excess NaBH4 (solid) was added in portion with vigorous stirring, during 30 min, until the initial dark red colour was discharged. The pale orange organic phase was separated and the aqueous phase extracted twice with dicholoromethane. The combined organic layers were dried on $Na_2SO_4$, filtered and evaporated under reduced pressure. The crude oil residue was purified by flash chromatography using ethyl acetate as eluent giving 794 mg of 6 as a pinkish oil.

Rf: 0.92 (AcOEt)

Yield: 90%

II-3 Bromination of Dihydrorhodamine B Hexyl Ester (6)

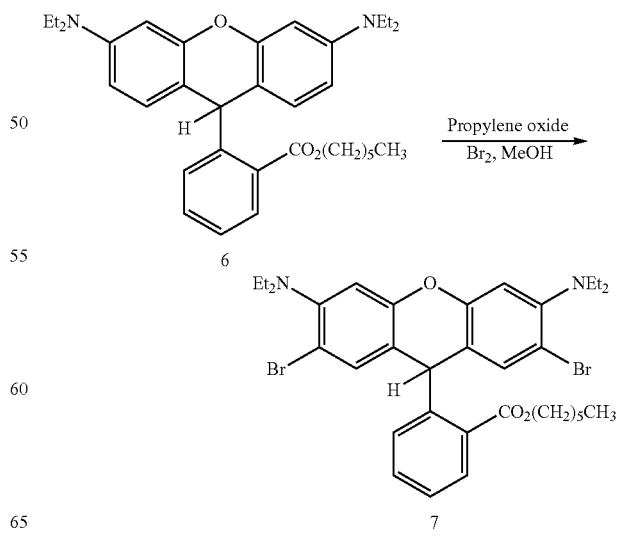

In a 100 ml round bottom flask we introduced dihydrorhodamine B hexyl ester (6) 784 mg (1.48 mmol) and 25 ml of methanol spectrograde. The mixture was stirred at room temperature until all the ester was dissolved. Propylene oxide 2 eq. (208 μL, 2.96 mmol) was added followed by dropwise addition of bromine 2 eq. (152 SL, 2.96 mmol). The stirring was continued at room temperature for 1 h 30 min. The volatile solvent were evaporated under reduced pressure and the red oily residue was subjected to purification by flash chromatography using ethyl acetate and hexanes (0.25: 9.75) as eluent to afford 207 mg of pure compound 2 as white foam solid and 123 mg of impur product.

Rf: 0.61 (AcOEt: Hexanes 0.5: 9.5)
Yield: 20.5%

II-4 Oxydation of the 27-dibromodihydrorhodamine B Hexyl Ester and Formation of the Acetate Salt of 2,7-dibromorhodamine B Hexyl Ester (8)

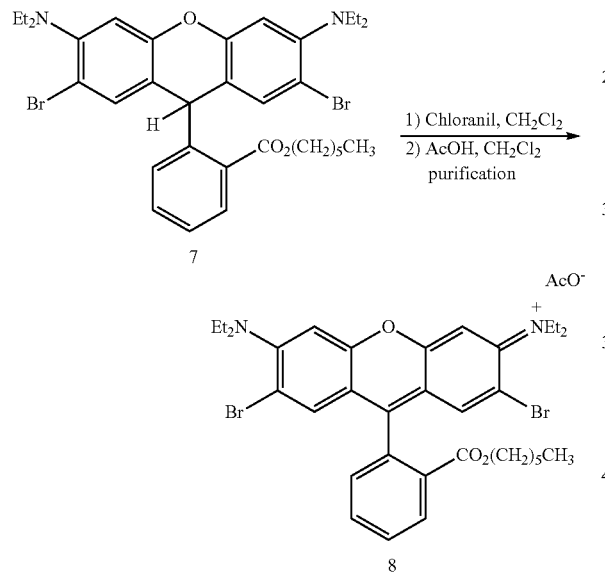

To a stirred solution of 2,7-dibromo dihydro rhodamine B hexyl ester 207 mg (0.30 mmol) in 8 ml of dichloromethane was added chloranil (1.2 eq., 0.36 mmol, 89 mg). The reaction mixture was stirred at room temperature overnight, then the reaction was stopped and the solvent was evaporated under reduced pressure to give a purple residue. The oxidized compound obtained in the precedent step was dissolved in 8 ml of dichloromethane and acetic acid (0.8 ml) was added dropwise. The clear red solution obtained was stirred for 5 min at room temperature followed by the evaporation of the volatile solvent under reduced pressure to give a purple viscous residue, which is purified by flash chromatography using a 10% methanol in dichloromethane as eluent to give the desired compound 8 as a viscous purple solid (198 mg).

Rf: 0.47 (MeOH: $CH_2Cl_2$ 1:9)
Yield: 86.9%
Nmr: ($CD_3OD$) δ 8.29 (dd, J=1.5 and 7.6 Hz, 1H); 7.82 (m, 2H); 7.40 (dd, J=1.6 and 7.2 Hz, 1 H); 7.37 (s, 2H); 7.28 (s, 2H); 3.96 (t, J=7.2 Hz, 2H);
3.72 (q, J=7.05 Hz, 8H); 1.91 (s, 3H); 1.29 (t, J=7.06 Hz, 12H); 1.08 (m, 4H); 0.79 (t, J=7.04 Hz, 3H)

Ms (FAB): Calculated for $C_{34}H_{42}O_3N_2Br_2$ (MH-AcO)$^+$: 684.1561

Found: 684.1587

UV (MeOH): $\lambda_{max}$ 582 nm

Example III

III Synthesis of 2'-(6-dimethylamino-3-dimethylimino-3H-xanthen-9-yl) 4',5'-dichloro-benzoic Acid Methyl Ester Hydrochloride (10)

III-1 Preparation of 2'-(6-dimethylamino-3-dimethylimino-3H-xanthen-9-yl) 4',5'-dichloro-benzoic Acid Hydrochloride (9)

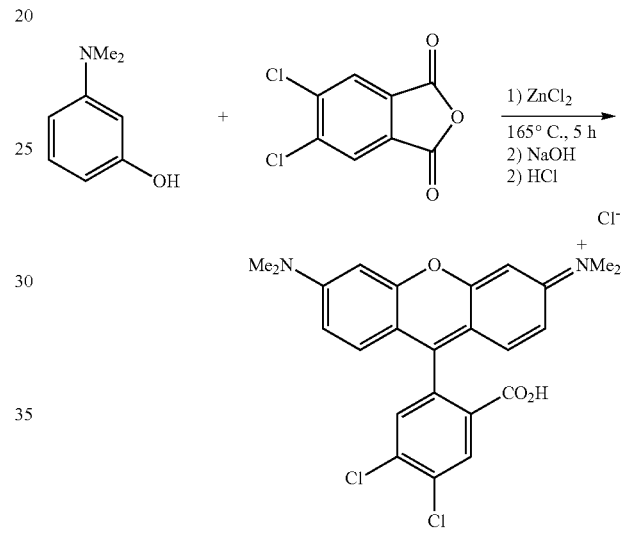

A mixture of 3.00 g (21.8 mmol) of 3-(dimethylamino) phenol, 3.00 g (13.8 mmol) of 4,5-dichlorophtalic anhydride, and 1.72 g of zinc chloride is heated in an oil bath at 165-170° C. for 5 h 30 min with stirring. The melt is cooled and powdered to give a red solid. The solid is washed with hot water, triturated with 10% sodium hydroxide and diluted with water. The gum which separates is collected, washed with more sodium hydroxide and water. The resulting dye base is then triturated with concentrated hydrochloride acid. Water was then added and the red precipitate obtained was collected and dried. The dye was then dissolved in methanol and precipitated with diethyl ether to give 9 as red solid (3.27 g).

Rf: 0.48 (MeOH: $CH_2Cl_2$ 2:8)
Yield: 48%
Nmr: ($CD_3OD$) δ 8.47 (s, 1H); 7.72 (s, 1H); 7.22 (d, J=9.47 Hz, 2H); 7.11 (m, 2H); 7.01 (d, J=2.4 Hz, 2H); 3.32 (s, 12H)

Ms (FAB): Calculated for $C_{24}H_{21}O_3N_2Cl_2$ (M-Cl)$^+$: 455.0929

Found: 455.0938

UV (MeOH): $\lambda_{max}$ 511 nm

III-2 Preparation of 2'-(6-dimethylamine-3-dimethylimino-3H-xanthen-9-yl) 4', 5-dichloro-benzoic Acid Methyl Ester Hydrochloride (10)

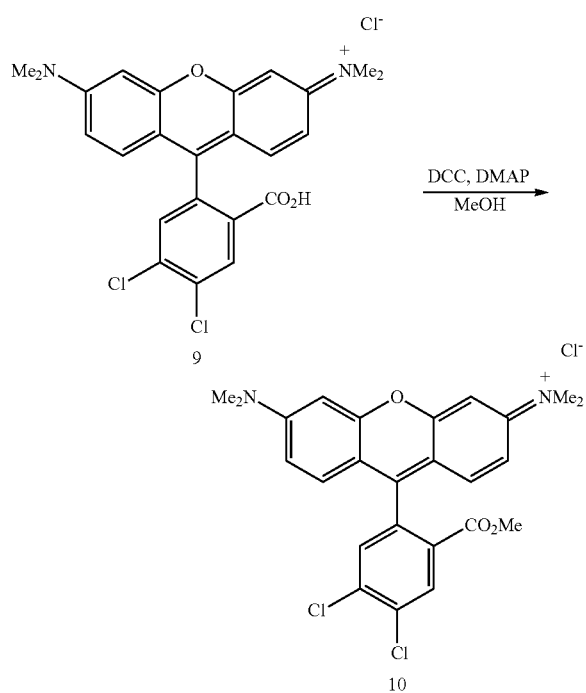

To a 250 ml round bottom flask, equipped with a magnetic stirrer, was added 738 mg (1.50 mmol) of the acid 9 and 40 ml of anhydrous dichloromethane and 10 ml of anhydrous DMF. The mixture was stirred under nitrogen until all the acid was dissolved. An amount of 309 mg (1.50 mmol) of 1,3-dicyclohexylcarbodiimide (DCC) was then added followed by 200 μL of methanol and 18 mg of 4-N,N-dimethylamino pyridine (DMAP). The mixture was stirred at room temperature overnight. The solvent was then distilled under reduced pressure to give a red residue, which was purified by flash chromatography using MeOH: $CH_2Cl_2$ (1.2:8.8) as eluant to afford 10 as red brown solid (350 mg).

Rf: 0.52 (MeOH: $CH_2Cl_2$ 2:8)
Yield: 46%
Nmr: ($CD_3OD$) δ 8.50 (s, 1H); 7.80 (s, 1H); 7.18 (d, J=9.2 Hz, 2H); 7.12 (m, 2H); 7.04 (d, J=2.31 Hz, 2H); 3.80 (s, 3H); 3.35 (s, 12H)
Ms (FAB): Calculated for $C_{25}H_{23}O_3N_2Cl_2$ (M-Cl)$^+$: 469.1085
Found: 469.1078
UV (MeOH): 555 nm

Example IV

IV Preparation of 45-dibromorhodamine 6G (11)

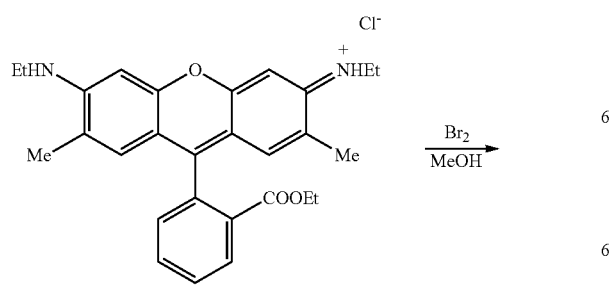

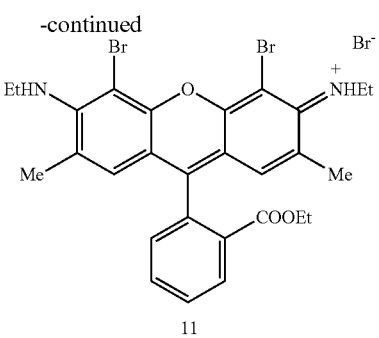

To a quantity of 600 mg (1.25 mmol) of rhodamine 6G dissolved in 50 ml of methanol was added dropwise, at room temperature, a solution of 128 L (2 eq., 2.50 mmol) of bromine. A precipitate was formed 10 min after the addition of the bromine. The mixture was stirred for 3 hours, and the solvent was evaporated under reduced pressure to give a red solid. The crude was recrystallized from methanol: diethyl ether (80 ml: 400 ml) to give the product 11 as green red solid (585 mg).

Rf: 0.26 (MeOH: $CH_2Cl_2$ 1:9)
Yield: 68.5%
Nmr ($CD_3OD$): δ 8.36 (dd, J=1.13 and 7.44 Hz, 1H); 7.89 (m, 2H); 7.47 (dd, J=1.46 and 6.76 Hz, I H); 6.98 (s, 2H); 4.07 (m, 6H); 2.29 (s, 6H); 1.28 (t, J=7.04 Hz, 6H); 1.02 (t, J=7.05 Hz, 3H)
Ms (FAB): Calculated for $C_{28}H_{30}O_3N_2Br_2$ (MH-Br)$^+$: 600.0623
Found: 600.0605
UV (MeOH): $\lambda_{max}$ 546 nm

Example V

V Synthesis of 4,5-dibromorhodamine 110 2-(2-methoxy Ethoxy) Ethyl Ester (13)

V-I Preparation of Rhodamine 110 2-(2-methoxy Ethoxy) Ethyl Ester (12)

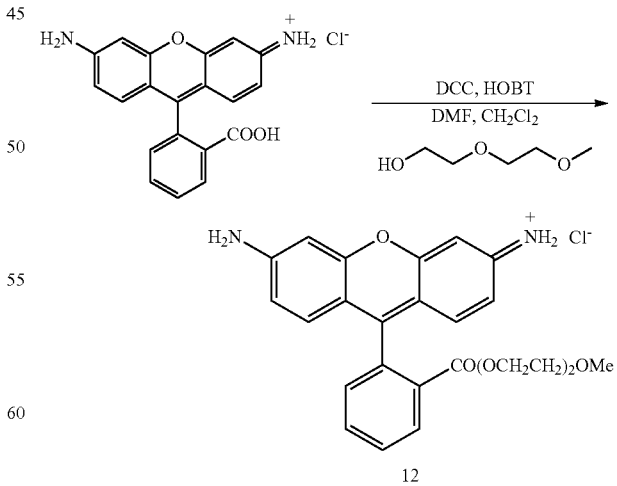

To Rhodamine 110 1.00 g (2.72 mmol) was added a mixture of anhydrous DMF and dichloromethane (60 ml: 10 ml) and the mixture was stirred until all the dye was dissolved. 1,3-dicyclohexylcarbodiimide (DCC) 562 mg (1 eq., 2.72 mmol) was added followed by HOBT 368 mg (1 eq., 2.72 mmol), 2-(2-methoxy ethoxy) ethanol 518 μL (1.60 eq., 4.36 mmol) and 33 mg (0.27 mmol) of 4-dimethylamino pyridine (DMAP). The reaction was stirred at room temperature overnight, and DMF was then distilled under reduced pressure to give a deep red residue. This residue was subjected to purification by flash chromatography using methanol: dichloromethane (2:8) as eluent to give (530 mg) of a red solid. Thin layer chromatography (TLC) showed the presence of another product with the desired one. The solid obtained was then dissolved in methanol (10 ml) and diethyl ether was added until a precipitate was obtained. The product was collected and dried to give the desired compound 12 (220 mg) as a red solid.

Rf: 0.33 (MeOH: CH$_2$Cl$_2$ 2:8)

Yield: 18.4%

Ms (FAB): Calculated for $C_{25}H_{25}N_2O_5$ (M-Cl)$^+$: 433.1736

Found: 433.1777

V-2 Preparation of 4, 5-dibromo Rhodamine 110 2-(2-methoxy Ethoxy) Ethyl Ester 13

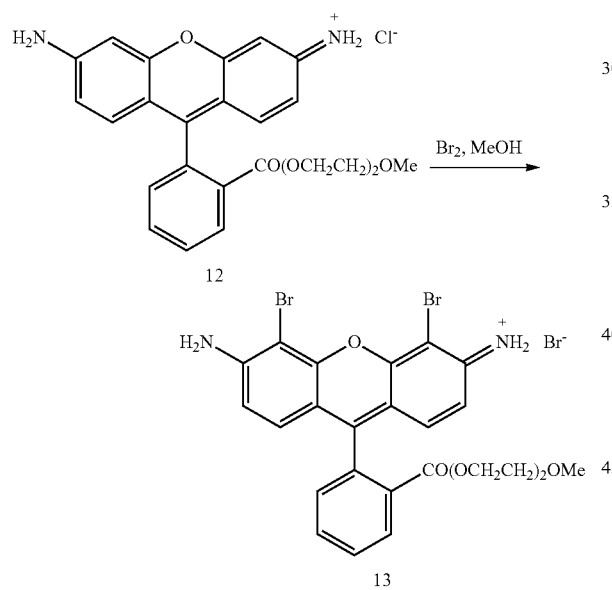

To a 100 ml round bottom flask, equipped with a magnetic stirrer, was added 235 mg (0.50 mmol) of the rhodamine 110 2-(2-methoxy ethoxy) ethyl ester 12 and 15 ml of methanol spectrograde. The mixture was stirred until all the rhodamine dye was dissolved. An amount of 50 μL (2 eq., 1.00 mmol) of bromine was then added, and the reaction was stirred at room temperature for 1 h 30 min. At the end of the reaction 10 μL of cyclohexene was added and the mixture was stirred for another 10 min. The volatile solvent was evaporated under reduced pressure to give a red solid. This solid was chromatographed on silica gel using MeOH: CH$_2$Cl$_2$ (1.2:8.8) as eluting solvent.

The pure fractions were combined and evaporated to give compound 13 (250 mg) as red solid.

Rf: 0.76 (MeOH: CH$_2$Cl$_2$ 2:8)

Yield: 74.3%

Nmr (CD$_3$OD): δ 8.38 (dd, J=1.5 and 6.87 Hz, 1H); 7.88 (m, 2H); 7.47 (dd, J=1.48 and 7.02 Hz, 1H); 7.15 (d, J=9.22 Hz, 2H); 7.04 (d, J=9.21 Hz, 2H);

4.15 (m, 2H); 3.39-3.25 (m, 9H)

Ms (FAB): Calculated for $C_{25}H_{23}O_5N_2Br_2$ (M-Br)$^+$: 588.9973

Found: 588.9962

UV (MeOH): λ$_{max}$ 502 nm

Example VI

VI Preparation of Rhodamine B 3-bromopropyl Ester (14)

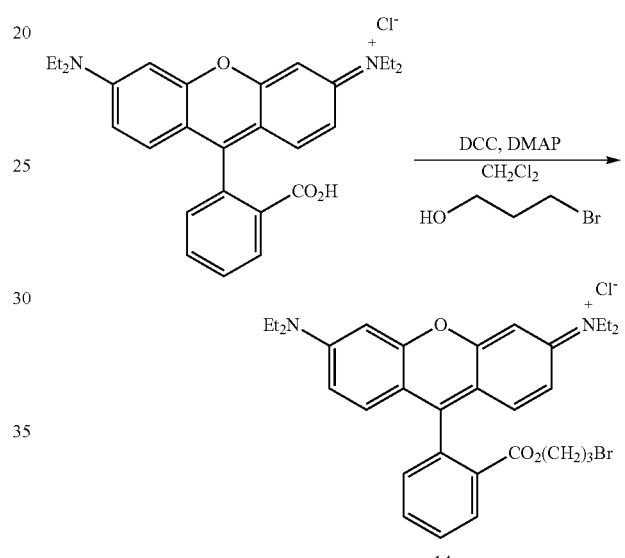

To Rhodamine B 300 mg (0.62 mmol) was added 5 ml of dichloromethane and the mixture was stirred until all the dye was dissolved. An amount of 1,3-dicyclohexylcarbodiimide (DCC) 142 mg (1 eq., 0.62 mmol) was added followed by 139 mg (10.0 mmol) of 3-bromopropanol and 8 mg (0.06 mmol) of 4-dimethyl aminopyridine (DMAP). The reaction was stirred at room temperature overnight. The N,N-dicyclohexyl urea was filtered and the solvent evaporated in vacuuo to give a deep red residue which was subjected to purification on flash chromatography using methanol: dichloromethane (1:9) as eluent. The fractions containing the desired compound were combined and and the solvent evaporated under reduced pressure to give 14 as a deep red viscous solid (300 mg)

Rf: 0.71 (MeOH: CH$_2$Cl$_2$ 1.5: 8.5)

Yield: 79.8%

Nmr (CD$_3$OD): δ 8.29 (m, I H); 7.85 (m, 2H); 7.43 (m, 1H); 7.06 (m, 6H); 4.08 (m, 2H); 3.68 (q, J=7.06 Hz, 8H); 3.21 (m, 2H); 1.81 (m, 1H); 1.29 (t, J=7.08 Hz, 12H)

Ms (FAB): Calculated for $C_{31}H_{36}O_3N_2Br_1$ (M-Cl)$^+$: 563.1909

Found: 563.1921

UV (MeOH): λ$_{max}$ 545 nm

Example VII

VII Synthesis of 2,7-dibromo-4'-carboxytetramethylrosamine Methyl Ester Acetate Salt (18)

VII-1 Preparation of 4'-carboxydihydrotetrametylrosamine Methyl ester (17)

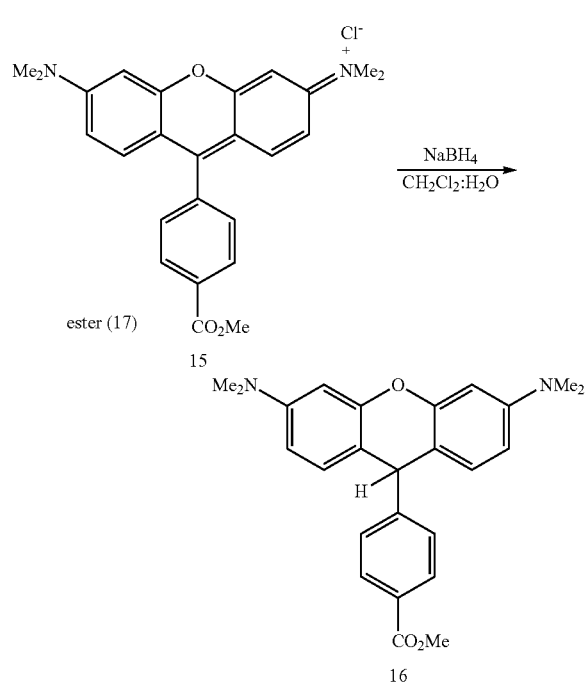

16

Ester 15 910 mg (2.08 mmol) was dissolved in 250 ml of dichromethane and 150 ml of water. Excess NaBH$_4$ (solid) was added in portion with vigorous stirring, during 30 min, until almost all color was discharged. The pale orange organic phase was separated and the water phase extracted twice with dicholoromethane. The combined organic layers were dried on Na$_2$SO$_4$, filtered and evaporated under reduced pressure. The crude oil residue was purified by flash chromatography using ethyl acetate as eluent, giving 530 mg of white foam solid.
Rf: 0.83 (AcOEt)
Yield: 63%

VII-2 Bromination of dihydro-4'-carboxytetramethylrosamine Methyl Ester (16)

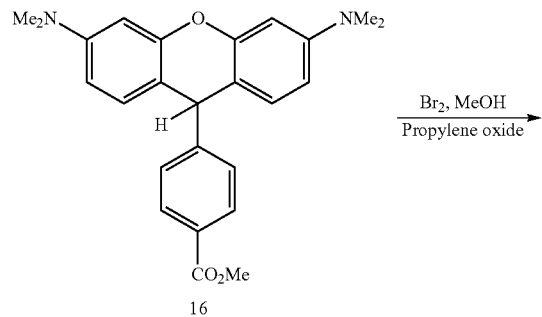

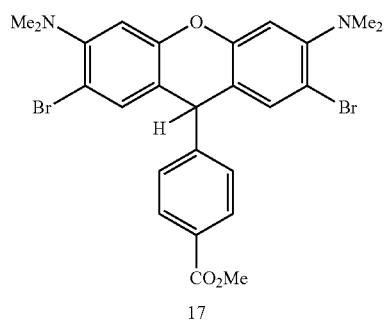

17

In a 100 ml round bottom flask we introduced dihydro rhodamine B hexyl ester 530 mg (1.31 mmol) and 50 ml of methanol spectrograde. The mixture was stirred at room temperature until all the ester was dissolved. Propylene oxide 2 eq. (185 μL, 2.63 mmol) was added followed by dropwise addition of bromine 2 eq. (135 μL, 2.63 mmol). The stirring was continued at room temperature for 1 h 30 min. The volatile solvent were evaporated under reduced pressure and the red oily residue was subjected to purification on flash chromatography using ethyl acetate and hexanes (1:9) as eluent to give a white foam solid (391 mg).

Rf: 0.36 (AcOEt:Hexanes 1:9)
Yield: 53.5%
Nmr (CD$_3$OD): δ 7.96 (d, J=8.5 Hz, 2H); 7.28 (d, J=8.31 Hz, 2H); 7.22 (s, 2H);
6.94 (s, 2H); 3.87 (s, 3H); 2.77 (s, 12H)

VII-3 Oxydation of the 2,7-dibromodihydro-4'-carbomexytetramethyl Rosamine Methyl Ester (17) and Formation of the Acetate Salt of 2,7 Dibromo-4'-Carboxytetramethylrosamine Methyl Ester (18)

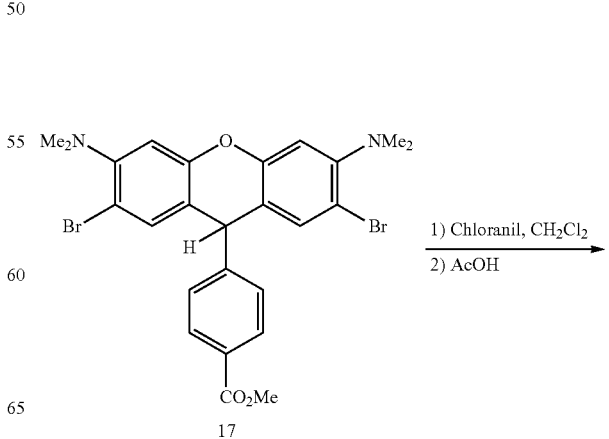

Example VIII

Preparation of 4, 5-dibromo Rhodamine B Lactone (19)

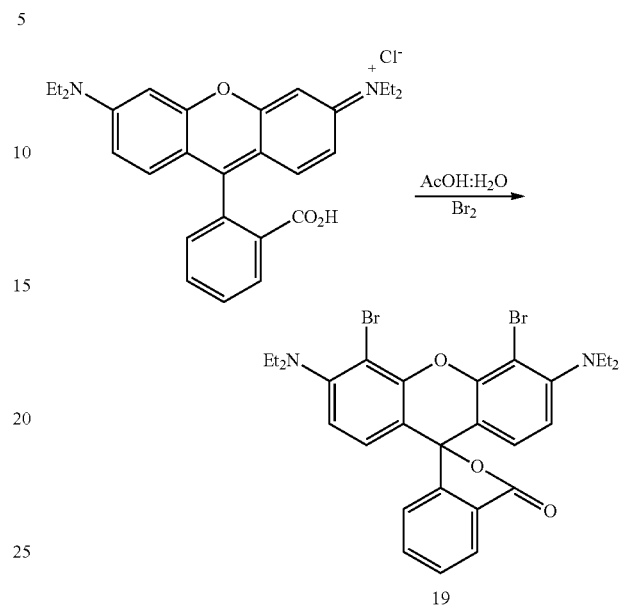

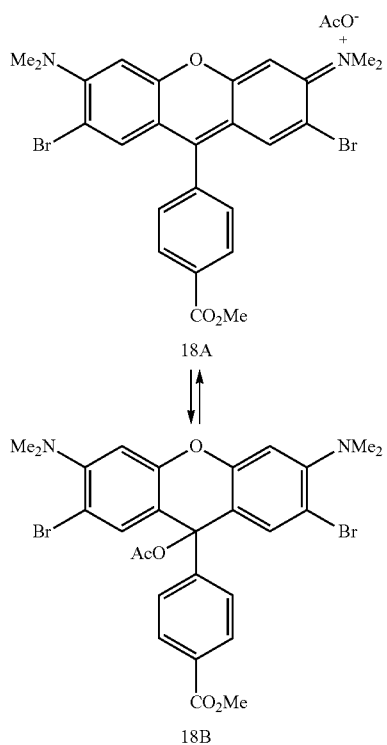

To a stirred solution of 2, 7-dibromodihydrotetramethylrhodamine methyl ester 390 mg (0.69 mmol) in 15 ml of dichloromethane was added chloranil (1.2 eq., 0.83 mmol, 205 mg). The reaction mixture was stirred at room temperature overnight, then the reaction was stopped and the solvent was evaporated under reduced pressure to give a purple residue. The oxidized compound obtained was dissolved in 15 ml of dichloromethane and acetic acid (0.8 ml) was added dropwise which. The clear purple solution obtained was stirred for 5 min at room temperature followed by the evaporation of the volatile under reduced pressure to give a purple viscous residue, which is purified by flash chromatography using a 10% methanol in dichloromethane as eluent to give the desired compound 18A which is in equilibrium with compound 18B.

18A Rf: 0.34 (MeOH: CH$_2$Cl$_2$ 1:9)

18B Rf: 0.93 (MeOH: CH$_2$Cl$_2$ 1:9)

Yield: 30%

Nmr (CD$_3$OD): δ 7.97 (d, J=8.28 Hz, 2H); 7.45 (d, J=8.33 Hz, 2H); 7.19 (s, 2H); 6.99 (s, 2H); 3.89 (s, 3H); 2.93 (s, 2, 64H); 2.83 (s, 12H); 2.01 (s, 0, 356H)

Ms (FAB): Calculated for C$_{25}$H$_{24}$O$_3$N$_2$Br$_2$ (MH-AcO)$^+$: 558.0153

Found: 558.0169

Rhodamine B 500 mg (1.04 mmol) was dissolved in 25 ml of acetic acid and 25 ml of water. Bromine 107 μL (2 eq., 2.08 mmol) was then added dropwise and the reaction mixture was then stirred at room temperature overnight. The water and the acetic acid were evaporated under reduced pressure and the residue obtained was redissolved in dichloromethane and 10% aqueous solution of sodium bicarbonate.

The organic layer was separated and washed twice with water, dried on Na$_2$SO$_4$, filtered and evaporated to give a pink oil. The residue was chromatographed on silica gel using methanol: dichloromethane (0.2:9.8) as eluent to give 544 mg of white foam solid.

Rf: 0.88 (MeOH: CH$_2$Cl$_2$ 1:9)

Yield: 86.8%

Nmr (CD$_3$OD) S 7.89 (dd, J=1.45 and 7.8 Hz, 1H); 7.62 (m, 2H); 7.14 (dd, J=1.6 and 7.2 Hz, 1H); 6.81 (d, J=9.2 Hz, 2H); 6.58 (d, J=9.2 Hz, 2H); 3.02 (q, J=7.05 Hz, 8H); 0.93 (t, J=7.04 Hz, 12H)

Ms (FAB): Calculated for C$_{28}$H$_{29}$O$_3$N$_2$Br$_2$ (MH)$^+$: 599.0545

Found: 599.0527

Example IX

Preparation of 2,7-dibromo Rhodamine B Lactone (20)

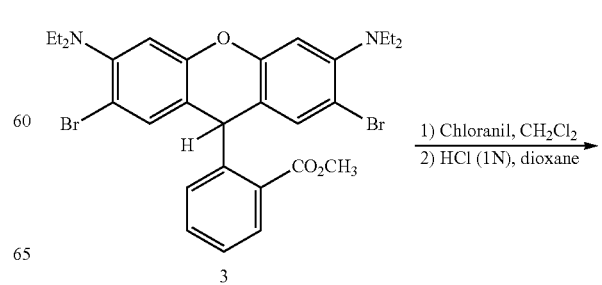

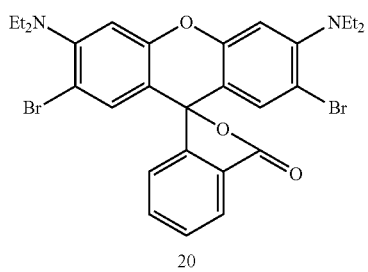

20

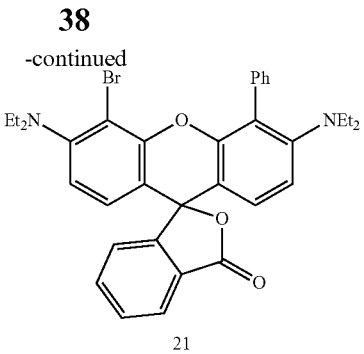

21

A stirred mixture of 10 mmole of the dibromolactone 19, 10 mmol of phenylboronic acid, 4.2 mL (30 mmol) of $Et_3N$, 0.067 g (0.3 mmole) of Pd $(OAc)_2$, and either 0.19 g (0.62 mmol) of tri-o-tolylphosphine catalyst or 0.16 g (0.62 mmol) of $PPh_3$ catalyst, in 40 mL of DMF is heated under a nitrogen atmosphere to 100 C for 2-3 hours. The solvent is then distilled off under reduced pressure, and the residue partitioned between $CH_2Cl_2$ and 10% aqueous $NH_3$. The organic extracts are then dried ($MgSO_4$) and concentrated under reduced pressure. Purification by flash chromatography on silica gel affords the pure monobromolactone 21. (See W. J. Thompson and J. Gaudino, *J. Org. Chem.* 1984, 49, 5237-5243; N. Miyaura, T. Yanagi, and A. Suzuki, *Synthetic Communications*, 1981, 11(7), 513-519).

To a stirred solution of 2, 7-dibromodihydrorhodamine B methyl ester (3) 46 mg (0.10 mmol) in 4 ml of dichloromethane was added chloranil (1.2 eq., 0.12 mmol, 30 mg). The reaction mixture was stirred at room temperature overnight, then the reaction was stopped and the solvent was evaporated under reduced pressure to give a purple residue. The oxidized compound obtained in the precedent step was dissolved in 4 ml of dioxane and HCl (1M) (5 ml) was added dropwise, and the resulting solution was wormed in water bath to give a clear red solution. After evaporation to dryness under reduced pressure we obtained a purple viscous residue. The residue was purified by flash chromatography using a ethyl acetate: hexanes (1.5:8.5) as eluent to give the desired compound 4 as a white foam solid (35 mg).

Rf: 0.34 (AcOEt: hexanes 1.5: 8.5)

Yield: 80%/o

Nmr: (CD3OD) δ 7.92 (dd, J=1.45 and 7.5 Hz, 1H) 7.63 (m, 4H); 7.18 (dd, J=1.6 and 7.2 Hz, I H); 7.02 (m, 2H).

Ms (FAB): Calculated for $C_{25}H_{29}O_3N_2Br_2$ $(MH)^+$: 599.0545

Found: 599.0570

Examples of Uses of the Rhodamine Derivatives According to the Invention as Intermediates Example X X Synthesis of 4-bromo-5-phenyl Rhodamine B Methyl Ester Chloride (22) X-1 Preparation of 4-bromo-5-phenyl Rhodamine B Lactone (21)

X-2 Preparation of 4-bromo-5-phenyl Rhodamine B Methyl Ester Chloride (22)

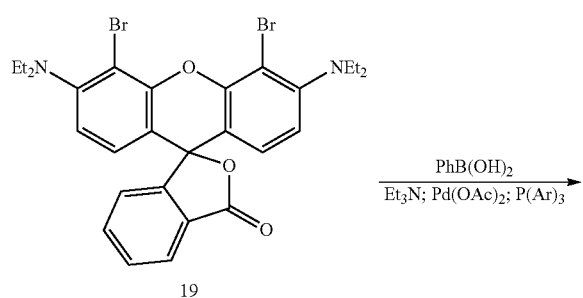

19

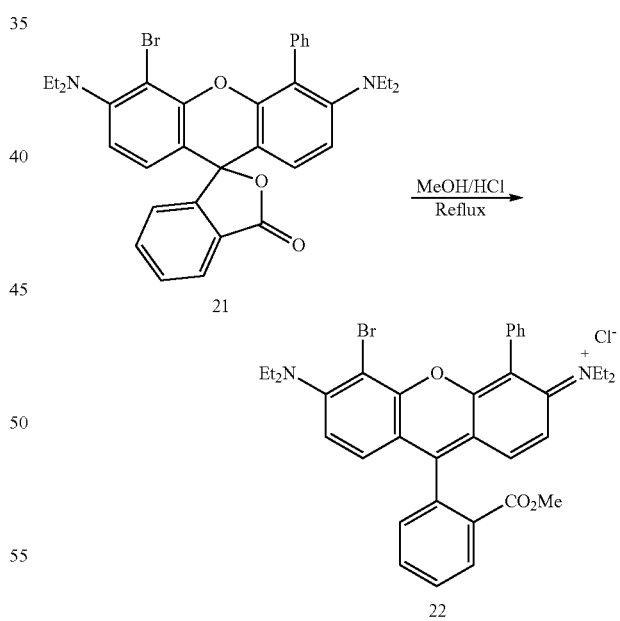

Methanolysis and concomitant oxidation of monobromolactone 21 is carried out by first stirring a mixture of 3-4 mmoles the compound in 100 mL of methanol while bubbling in a fine stream of anhydrous HCl gas for a period of 45 min and then heating the mixture to reflux overnight. The methanol is then evaporated under reduced pressure and the dark red residue purified by flash chromatography to afford the desired dark red product 22.

Example XI

XI Synthesis of 2,7-dibromo-4,5-dimethyl Rhodamine B Methyl Ester Bromide (24)

XI-1 Preparation of 4,5-dimethyl Rhodamine B Lactone (23)

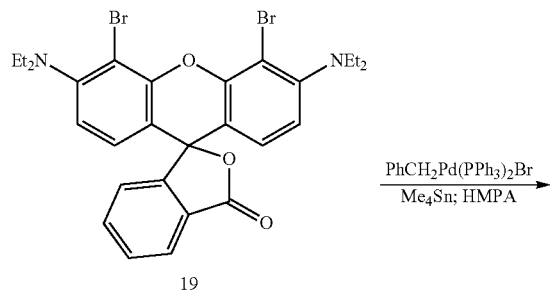

To a solution of 7.0 mmol of the dibromolactone 19 in hexamethylphosphoramide (HMPA) is added 0.05 mmol of the catalyst benzylbromobis (triphenylphosphine)-palladium (11) and 16.0 mmol of tetramethyltin. The solution is then heated to 65° C. with stirring under air in a sealed tube until blackening occurs. The solution is then cooled to room temperature and 5 mL of water is added. The mixture is extracted with dichloromethane and the organic solution dried over $MgSO_4$. Evaporation of the solvent yields the crude product which is purified by flash chromatography on silica gel to give the pure lactone 23. (See D. Milstein and J. K. Stille, *J. Amer. Chem. Soc.* 1979, 101 (17), 4992-4998).

XI-2 Preparation of 2, 7-dibromo-4, 5-dimethyl Rhodamine B Methyl Ester Bromide (24)

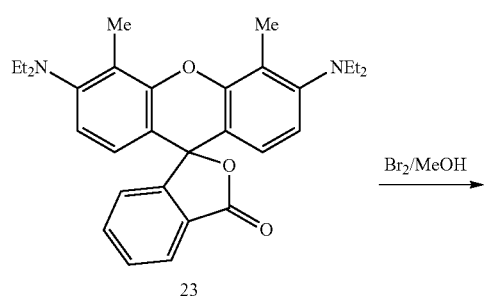

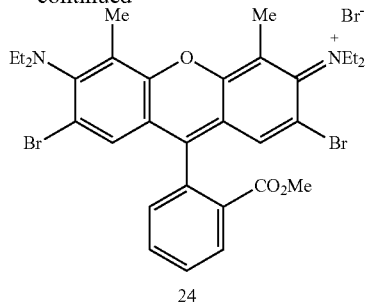

A solution of 1.25 mmol 4,5-dimethyl Rhodamine B lactone 23 in 50 ml methanol was treated, at room temperature, by 2.5 mmol of bromine. A precipitate was formed after the addition of bromine and the mixture was stirred for 3 hours. The solvent was evaporated under reduced pressure to give a red solid which was recrystallized from methanol: diethyl ether to give the desired dibromomethyl ester 24.

Example XII

XII Synthesis of 2-bromo-7-ethynyl Rhodamine B Methyl Ester Bromide (26)

XII-I Preparation of 2-bromo-7-ethymyl Rhodamine B Lactone (25)

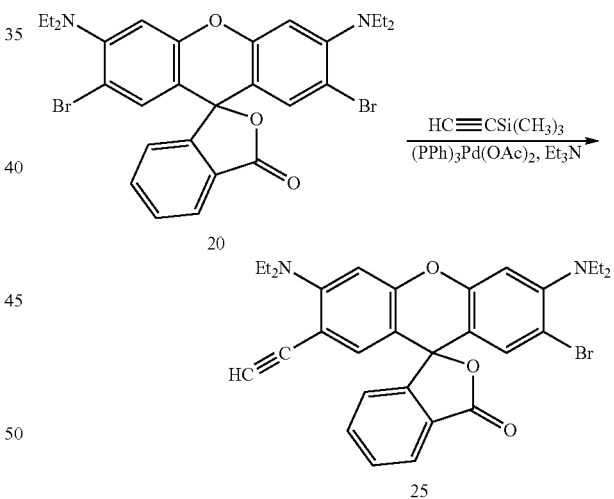

A mixture of 53 mmol dibromolactone 20 and 53 mmol of ethynyltrimethylsilane, 300 mg of triphenyl phosphine and 150 mg of palladium (II) acetate is prepared in 100 ml of deaerated anhydrous triethylamine at 30-40° C. The mixture is then heated under argon at 90-100° C. for 22 hours The mixture is cooled and filtered to give the desired impure trimethylsilyl derivative of 25. Treatment with potassium carbonate at 25° C. for 16 hours followed by neutralization gives lactone 25 after purification by flash chromatography. (See W. B. Austin, N. Bilow, W. J. Kelleghan, and K. S. Y. Lau. *J. Org Chem.* 1981, 46, 2280-2286; S. Takahashi, Y. Kuroyama, K. Sonogashira, N. Hagihara, *Systhesis,* 1980, 627-630).

XII-2 Preparation of 2-bromo-7-ethynyl Rhodamine B Methyl Ester Chloride (26)

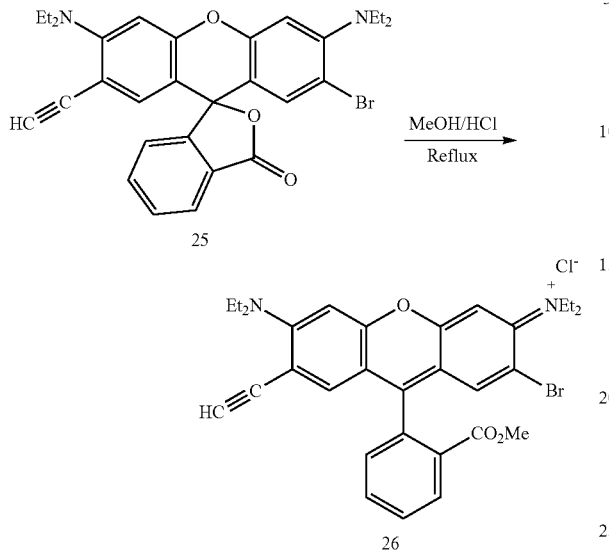

A stirred solution of 3.5 mmol of 2-bromo-7-ethynyl Rhodamine B lactone 25 in 100 mL of methanol is treated with a fine stream of bubbled HCl gas for 45 min. The reaction mixture is then heated to reflux overnight and the methanol evaporated under reduced pressure. The dark red residue is purified by flash chromatography using a mixture of methanol and dichloromethane to afford the desired ester 26.

Example XIII

XIII Synthesis of 4,5-dibromo-2,7-di-n-butyl Rhodamine B Methyl Ester Bromide (28)

XIII-1 Preparation of 2,7-di-n-butyl Rhodamine B Lactone (27)

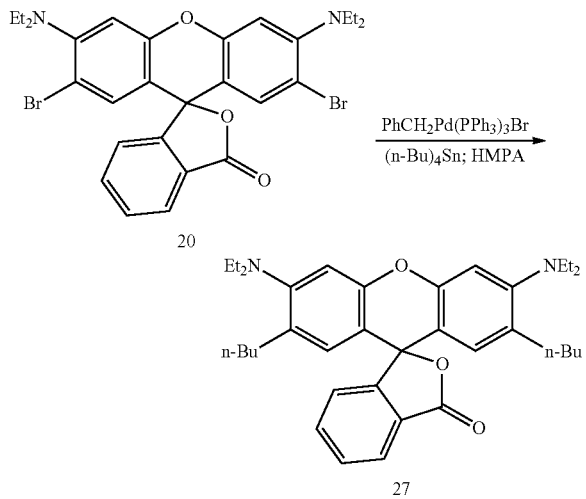

A solution of 7.0 mmol of the dibromolactone 20 in 4 ml hexamethylphosphoramide (HMPA) is treated with 0.05 mmol benzylbromobis (triphenylphosphine) palladium (II) and 16.0 mmol of tetra-n-butyltin compound. The solution is then heated to 65° C. with stirring under air in a sealed tube until blackening occurs. The solution in then cooled to room temperature and 5 ml of water is added. The mixture is extracted with dichloromethane and the latter is evaporated in vacuo to give the crude product which is purified by flash chromatography to yield the pure lactone 27. (See D. Milstein and J. K. Stille, *J Amer. Chem. Soc.* 1979, 101(17), 4992-4998).

XIII-2 Preparation of 4,5-dibromo-2,7-di-n-butyl Rhodamine B Methyl Ester Bromide (28)

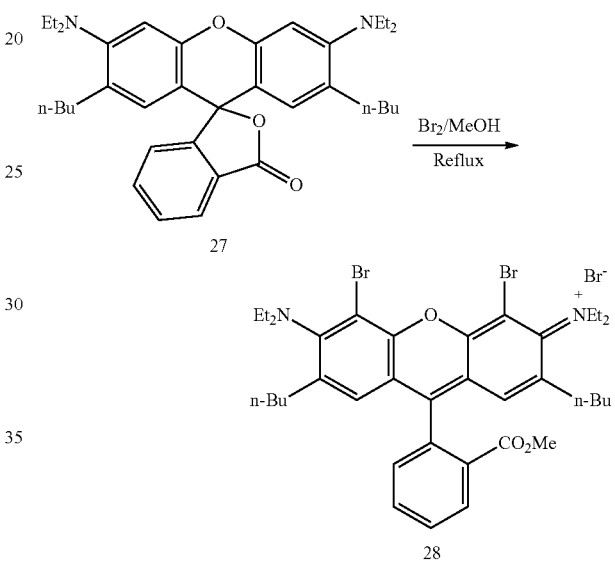

A solution of 1.25 mmol of Rhodamine B lactone 27 in 50 ml of methanol is treated, at room temperature, with 2.5 mmol of bromine. A precipitate is formed shortly after the addition of bromine and the mixture is stirred for 3 hours. The solvent is then evaporated under reduced pressure to give a red solid which is recrystallized from methanol: diethyl ether to give the desired dibromomethyl ester bromide 28.

Determination of the Bacteriosidic and/or Bacteriostatic of Rhodamine Derivatives Experimental Design The following experimental procedures have been used for the determination of antibacterial activity.

Bacteriostasis:

*Escherichia coli*: (0157)a

The protocol used for the bacteriosidic inactivation was performed as described in Brasseur and coll. with few modifications for bacteriosidic potential assessment (Brasseur et al, 2000). Compounds TH9402, HA-X-44, HA-X-164, HA-X-171 and HA-VIII-92 showed antibacterial activity against *E. coli* using the following experimental procedure.

Bacterial was grown overnight in Lubria Broth medium (LB), 100 μl ($\approx 1 \times 10^7$ bacteria) of each bacterial suspension was added to 4 ml of LB medium, a small aliquot of the bacterial suspension was taken out for bacterial titer prior to treatment expressed as CFU/mL (colony forming units per mL). To the bacterial suspension was added the rhodamines derivatives, each derivative being tested in duplicate at a concentration of 50 µM. Each mixture of bacteria rhodamine derivative was incubated at 37° C. for 40 minutes. The bacteria-rhodamine suspensions were then treated and exposed to a 514 nm wavelength light for 180 minutes, for a total output energy of 30 Joules/cm². Following the treatment time, the bacteria-rhodamine suspensions were centrifuged at 3000 g, resuspended in 4 ml and serial dilutions were performed for each duplicate. 10 µL of the diluted bacterial suspensions were plated, the plates incubated overnight at 37° C. The bacteriostatic effect is expressed by the number of CFU/mL.

*Pseudomonas aeruginosa:*

The protocol used for the bacteriosidic inactivation was performed as described in Brasseur and coll. with few modifications for bacteriosidic potential assessment (Brasseur et al, 2000). Compound TH9402 showed antibacterial activity against *P. aeruginosa* using the following experimental procedure.

Bacterial was grown overnight in Lubria Broth medium (LB), 100 µl (≈1×10⁷ bacteria) of each bacterial suspension was added to 4 ml of LB medium, a small aliquot of the bacterial suspension was taken out for bacterial titer prior to treatment expressed as CFU/mL. To the bacterial suspension was added the rhodamines derivatives, each derivative being tested in duplicate at a concentration of 50 µM. Each mixture of bacteria rhodamine derivative was incubated at 37° C. for 40 minutes. The bacteria-rhodamine suspensions were then treated and exposed to a 514 nm wavelength light for 180 minutes, for a total output energy of 30 Joules/cm². Following the treatment time, the bacteria-rhodamine suspensions were centrifuged at 3000 g, resuspended in 4 ml and serial dilutions were performed for each duplicate. 10 µL of the diluted bacterial suspensions were plated, the plates incubated overnight at 37° C. The bacteriostatic effect is expressed by the number of CFU/mL.

*Salmonella typhimurium*

The protocol used for the bacteriosidic inactivation was performed as described in Brasseur and coll. with few modifications for bacteriosidic potential assessment (Brasseur et al, 2000). Compounds TH9402, HA-X-44 and HA-X-164 showed antibacterial activity against *S. typhirrauriufn* using the following experimental procedure.

Bacterial was grown overnight in Lubria Broth medium (LB), 100 µl (≈×10⁷ bacteria) of each bacterial suspension was added to 4 ml of LB medium, a small aliquot of the bacterial suspension was taken out for bacterial titer prior to treatment expressed as CFU/mL. To the bacterial suspension was added the rhodamines derivatives, each derivative being tested in duplicate at a concentration of 50 µM. Each mixture of bacteria rhodamine derivative was incubated at 37° C. for 40 minutes. The bacteria-rhodamine suspensions were then treated and exposed to a 514 nm wavelength light for 180 minutes, for a total output energy of 30 Joules/cm². Following the treatment time, the bacteria-rhodamine suspensions were centrifuged at 3000 g, resuspended in 4 ml and serial dilutions were performed for each duplicate. 10 µL of the diluted bacterial suspensions were plated, the plates incubated overnight at 37° C. The bacteriostatic effect is expressed by the number of CFU/mL.

*Staphilococcus epidermitis*

The protocol used for the bacteriosidic inactivation was performed as described in Brasseur and coll. with few modifications for bacteriosidic potential assessment (Brasseur et al, 2000). Compounds TH9402, HA-X-40, HA-X-44, HA-X-149 and HA-X-164 showed antibacterial activity against *S. tryphimurium* using the following experimental procedure.

Bacterial was grown overnight in Lubria Broth medium (LB), 100 µl (≈1×10⁷ bacteria) of each bacterial suspension was added to 4 ml of LB medium, a small aliquot of the bacterial suspension was taken out for bacterial titer prior to treatment expressed as CFU/mL. To the bacterial suspension was added the rhodamines derivatives, each derivative being tested in duplicate at a concentration of 50 µM. Each mixture of bacteria rhodamine derivative was incubated at 37° C. for 40 minutes. The bacteria-rhodamine suspensions were then treated and exposed to a 514 nm wavelength light for 180 minutes, for a total output energy of 30 Joules/cm². Following the treatment time, the bacteria-rhodamine suspensions were centrifuged at 3000 g, resuspended in 4 ml and serial dilutions were performed for each duplicate. 10 µL of the diluted bacterial suspensions were plated, the plates incubated overnight at 37° C. The bacteriostatic effect is expressed by the number of CFU/mL.

*Staphilococcus epidermitis*

The protocol used for the bacteriosidic inactivation was performed as described in Brasseur and coll. with few modifications for bacteriosidic potential assessment (Brasseur et al, 2000). Compounds HA-X-171 and HA-VIII-92 showed antibacterial activity against *S. epidermitis* using the same experimental procedure except that a concentration of 10 µM was used in the experimental procedure.

Bacterial was grown overnight in Lubria Broth medium (LB), 100 µl (≈1×10⁷ bacteria) of each bacterial suspension was added to 4 ml of LB medium, a small aliquot of the bacterial suspension was taken out for bacterial titer prior to treatment expressed as CFU/mL. To the bacterial suspension was added the rhodamines derivatives, each derivative being tested in duplicate at a concentration of 50 µM. Each mixture of bacteria rhodamine derivative was incubated at 37° C. for 40 minutes. The bacteria-rhodamine suspensions were then treated and exposed to a 514 nm wavelength light for 180 minutes, for a total output energy of 30 Joules/cm². Following the treatment time, the bacteria-rhodamine suspensions were centrifuged at 3000 g, resuspended in 4 ml and serial dilutions were performed for each duplicate. 10 µL of the diluted bacterial suspensions were plated, the plates incubated overnight at 37° C. The bacteriostatic effect is expressed by the number of CFU/mL.

*Staphilococcus epidermitis*

The protocol used for the bacteriosidic inactivation was performed as described in Brasseur and coll. without modification for bacteriosidic potential assessment (Brasseur et al, 2000). Compound HA-X-40 showed antibacterial activity against *S. epidermitis* using the same experimental procedure except that an extrusion time of 90 minutes was performed prior to radiation treatment.

Bacterial was grown overnight in Lubria Broth medium (LB), 100 µl (≈1×10⁷ bacteria) of each bacterial suspension added to 4 ml of LB medium. A small aliquot of the bacterial suspension was taken out for bacterial titer prior to treatment. To the bacterial suspension was added the rhodamines derivatives, the derivative being tested in duplicate at a concentration of 50 µM. Each mixture of bacteria rhodamine derivative was incubated at 37° C. for 40 minutes. The bacterial suspensions were then centrifuged at 3000 g for 10 minutes, resuspended in 4 mL LB media and incubated for 90 minutes at 37° C. to allow extrusion of the derivatives. The bacteria rhodamines suspensions were then treated and exposed to a 514 nm wavelength light for 180 minutes, for a total output energy of 30 Joules/cm². Following the treatment time, serial dilutions were performed for each duplicate and 10 μL of the diluted bacterial suspension was plated, the plates incubated overnight at 37° C. The bacteriostasic effect is expressed by the number of colony forming units/mL.

Determination of the Antiviral Activity of the Rhodamine Derivatives of Formula (I)

Antiviral Assay:

References

Lin L., Inactivation of cytomegalovirus in platelet concentrates using Helix™ technology, Seminar in Hematology, 2001, 38, 4, Supp. #11, 27-33;

Brasseur, N., Ménard, I., Forget, A., El Jastimi, R., Hamel, R., Molfino, N. A. and E van Lier, J., Eradication of Multiple Myeloma and Breast Cancer Cells by Th9402-mediated Photodynamic Therapy: Implication of Clinical Ex vivo Purging of Autologous Stem Cell Transplant, Photochemistry and Photobiology, 2000, 72, 6, 780-878;

Lin. B., Londe, H., Janda, J. M., Hanson, C. V. and Corash, L., Photochemical Inactivation of Pathogenic, Bacteria in Human Platelet Concentrates, Blood, 1994, 83, 9, 2698-2706;

Lin. B. L., Londe, H., Hanson, C. V., Wiesehahn, G., Isaacs, S., Cimino, G. and Corash, L., Photochemical Inactivation of Cell-Associated Human Immunodeficiency Virus in Platelets Concentrates, Blood, 1993, 82, 1, 292-297;

Lin, B. L., Wiesehahn, G. P., Morel, P. A. and Corash L., Use of 8-Methoxypsoralen and Long-Wavelength Ultraviolet Radiation for Decontamination of Platelet Concentrates, Blood, 1989, 74, 1, 517-525.

Objective:

The antiviral assay was performed as described in Lin, L (2001). Human diploid fibroblast, foreskin cells (FS), were used in this assay. The anti-viral activity of rhodamines derivatives were tested and results showed that all compounds, HA-X 40, HA-X-149, HA-X-164, HA-X-171 and HA-VIII-92 followed by PDT treatment possess antiviral activity against Cytomegalovirus.

Method:

FS cells were grown to confluency in shell vials. At the time of infection 2.5-3.5×10 cells were growing on each coverslip. The CMV (AD169) stock solution containing 1 mL of virus were quickly thawed, seeded and diluted following 100 fold dilutions in MEM (Earle's salt) supplemented with L-glutamine and 2% FBS, total volume 30 ml.

The titer of the virus have been determined at $10^{-2}$ ($10^4$ $TCID_{50}$) plaque forming units (pfu) in 0.2 ml. Therefore 1 mL used in the PDT experiments represents $1.4 \times 10^5$ pfu. A M. O. I. of 0.4-0.5 of CMV was used throughout this experiment.

The plates containing no rhodamines derivatives were treated with light in parallel to the non-light treated plates. The concentration used throughout the assay for the rhodamines derivatives was maintained at 50 uM. Following the addition of the derivatives to the viral stock solution, the plates were placed into the Theralux L6.30 device and illuminated for 180 minutes with 210 rpm agitation. The energy output was measured to be 30 Joules/cm². The non-PDT plate was placed into a 37° C. incubator for the same amount of time. Following this treatment time, dilutions were made and inoculated with the FS cells under centrifugation (2000 g, 60 minutes). Following the centrifugation, the cells are incubated 60 minutes at 37° C., 5% CO2, then are washed with the culture media and incubated for 18-24 hours at 37° C. at 5% $CO_2$. Inoculation volume of each dilution was 0.2 ml, the dilutions made were $10^{-3}$ to $10^{-5}$ in duplicate.

The cells were fixed, removed from the vials and stained with labelled FITC (fluorescein isothiocyanate) Mab to CMV immediate early antigen.

CMV viral particles were counted. One fluorescent virus particle (kidney-shaped) represents one plaque forming unit.

Here is the protocol for the two other compounds TI-9402 and HA-X-44 which inhibit cytometalovirus infectivity without PDT treatment as well as a new version of the table to be added in the patent.

Objective:

The antiviral assay was performed as described in Lin, L (2001). Human diploid fibroblast, foreskin cells (FS), were used in this assay. The anti-viral activity of rhodamines derivatives were tested and results showed that compounds, TH9402 and HA-X-44 did not need PDT treatment to possess antiviral activity against Cytomegalovirus.

Method:

FS cells were grown to confluency in shell vials. At the time of infection 2.5-3.5×10 cells were growing on each coverslip. The CMV (AD169) stock solution containing 1 mL of virus were quickly thawed, seeded and diluted following 100 fold dilutions in MEM (Earle's salt) supplemented with L-glutamine and 2% FBS, total volume 30 ml.

The titer of the virus have been determined at $10^{-2}$ ($10^4$ $TCID_{50}$) plaque forming units (pfu) in 0.2 ml. Therefore 1 mL used in the PDT experiments represents $1.4 \times 10^5$ pfu. A M. O. I. of 0.4-0.5 of CMV was used throughout this experiment.

The plates containing no rhodamines derivatives were treated with light in parallel to the non-light treated plates. The concentration used throughout the assay for the rhodamines derivatives was maintained at 50 uM. Following the addition of the derivatives to the viral stock solution, dilutions were made and inoculated with the FS cells under centrifugation (2000 g, 60 minutes). Following the centrifugation, the cells are incubated 60 minutes at 37° C., 5% CO2, then are washed with the culture media and incubated for 18-24 hours at 37° C. at 5% $CO_2$. Inoculation volume of each dilution was 0.2 ml, the dilutions made were $10^{-3}$ to $10^{-5}$ in duplicate.

The cells were fixed, removed from the vials and stained with labelled FITC (fluorescein isothiocyanate) Mab to CMV immediate early antigen.

CMV viral particles were counted. One fluorescent virus particle (kidney-shaped) represents one plaque forming unit.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

What is claimed is:

1. A method for treating a tissue sample from a patient, comprising the steps of:
   harvesting the tissue sample from the patient, wherein the tissue sample is infected with bacteria, wherein the bacteria is gram positive;
   providing a rhodamine compound, wherein the rhodamine compound is 2'-(6-dimethylamino-3-dimethylimino-3H-xanthen-9-yl) 4', 5'-dichloro-benzoic acid methyl ester hydrochloride;
   mixing the rhodamine compound and the tissue sample to form a mixture, exposing the mixture to radiant energy to inhibit or kill the bacteria; and transplanting the exposed mixture into the patient.

2. The method of claim 1, wherein the bacteria is *Staphylococcus epidermitis*.

3. The method of claim 1, wherein the mixture is exposed to a wavelength of 514 nm.

4. The method of claim 1, wherein the tissue sample is blood.

5. The method of claim 1, wherein the tissue sample is bone marrow.

6. The method of claim 1, wherein the mixture is exposed to radiant energy for 180 minutes.

7. The method of claim 1, further comprising the steps of centrifuging the mixture;

resuspending the centrifuged mixture; and incubating the resuspended centrifuged mixture.

8. The method of claim 7, wherein the resuspended centrifuged mixture is incubated for 90 minutes.

9. The method of claim 7, wherein the resuspended centrifuged mixture is incubated before exposing the mixture to radiant energy.

\* \* \* \* \*